(12) United States Patent
Bono et al.

(10) Patent No.: US 12,290,275 B2
(45) Date of Patent: May 6, 2025

(54) ROTARY OSCILLATING AND RECIPROCATING SURGICAL TOOL

(71) Applicant: GLOBUS MEDICAL, INC., Audubon, PA (US)

(72) Inventors: Peter L. Bono, Bingham Farms, MI (US); James D. Lark, Orchard Lake, MI (US); John S. Scales, Clinton Township, MI (US)

(73) Assignee: Globus Medical, Inc., Audubon, PA (US)

( * ) Notice: Subject to any disclaimer, the term of this patent is extended or adjusted under 35 U.S.C. 154(b) by 483 days.

(21) Appl. No.: 17/718,563

(22) Filed: Apr. 12, 2022

(65) Prior Publication Data

US 2022/0338895 A1 Oct. 27, 2022

Related U.S. Application Data

(60) Provisional application No. 63/180,470, filed on Apr. 27, 2021.

(51) Int. Cl.
*A61B 17/32* (2006.01)
*A61B 17/00* (2006.01)

(52) U.S. Cl.
CPC .......... *A61B 17/32002* (2013.01); *A61B 2017/00398* (2013.01); *A61B 2017/00464* (2013.01); *A61B 2017/00477* (2013.01); *A61B 2017/00734* (2013.01)

(58) Field of Classification Search
CPC .............................................. A61B 17/32002
See application file for complete search history.

(56) References Cited

U.S. PATENT DOCUMENTS

2021/0361311 A1* 11/2021 Truckai ............ A61B 17/32002

\* cited by examiner

*Primary Examiner* — Olivia C Chang

(57) ABSTRACT

A surgical tool that has a pair of transmissions coupled to one another to effect driving of a cutting tool in both bidirectional intermittent rotational manners and in opposite directions of continuous rotation. The transmissions are driven by a motor coupled to one of the transmissions which is coupled to the second transmission.

19 Claims, 27 Drawing Sheets

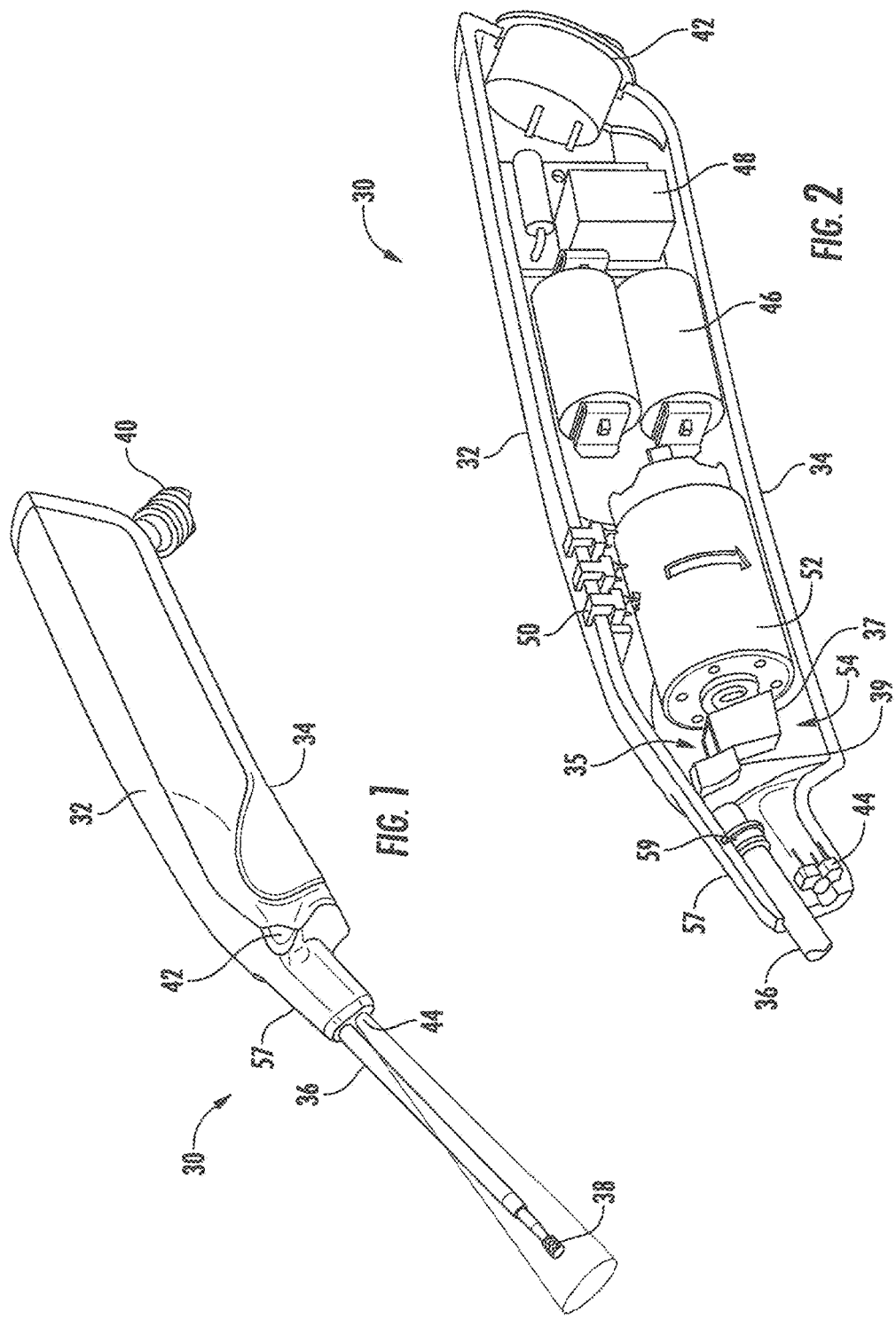

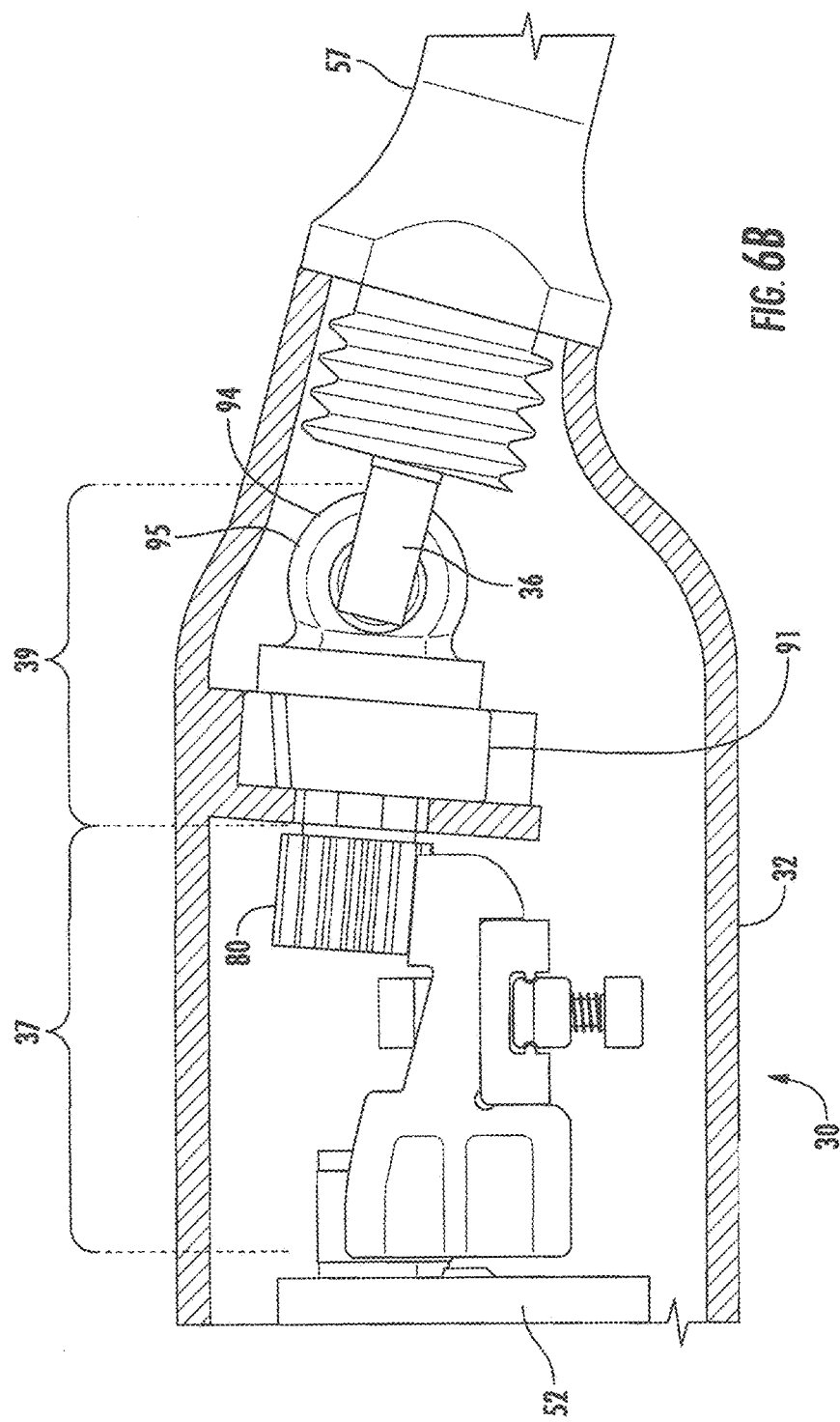

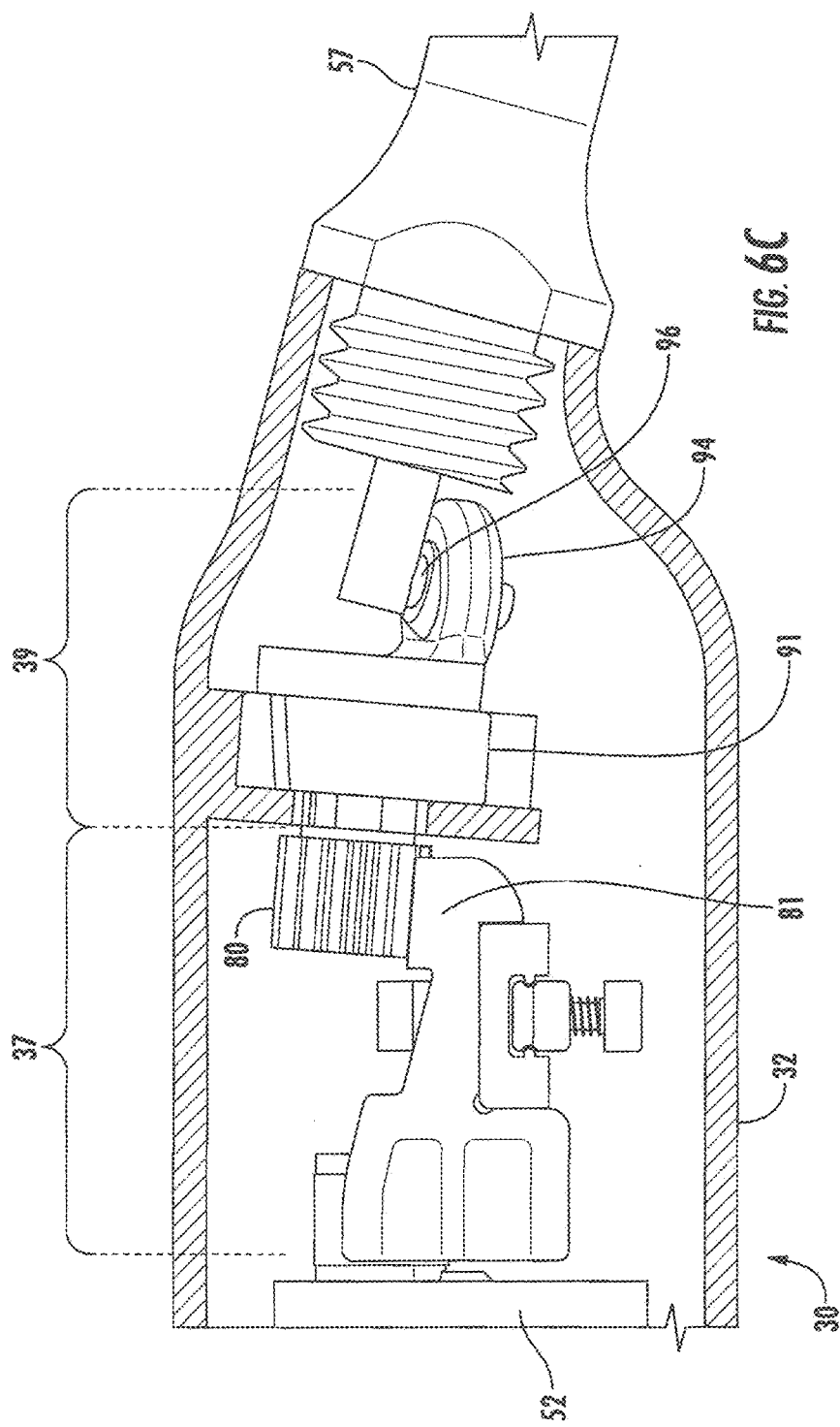

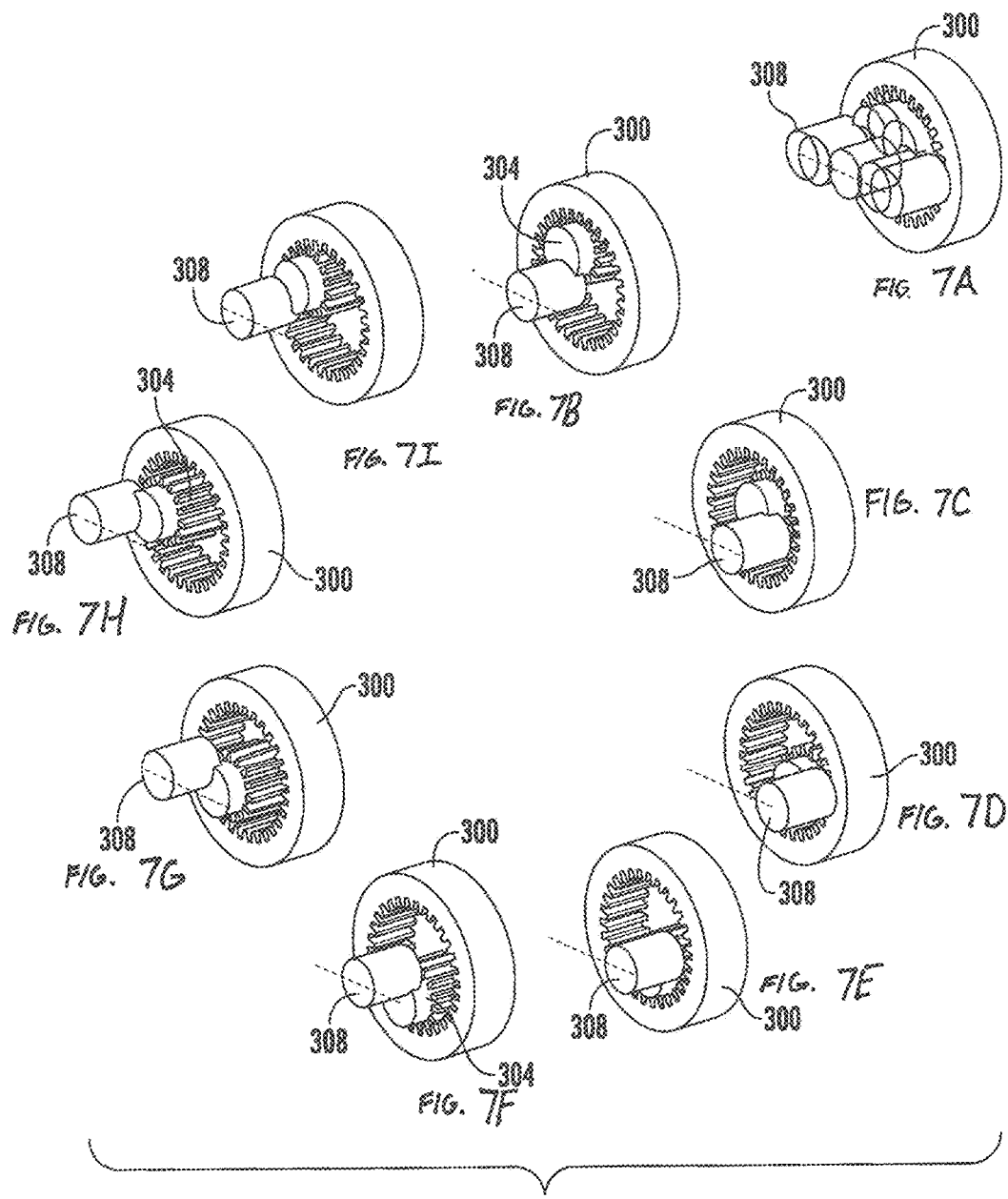

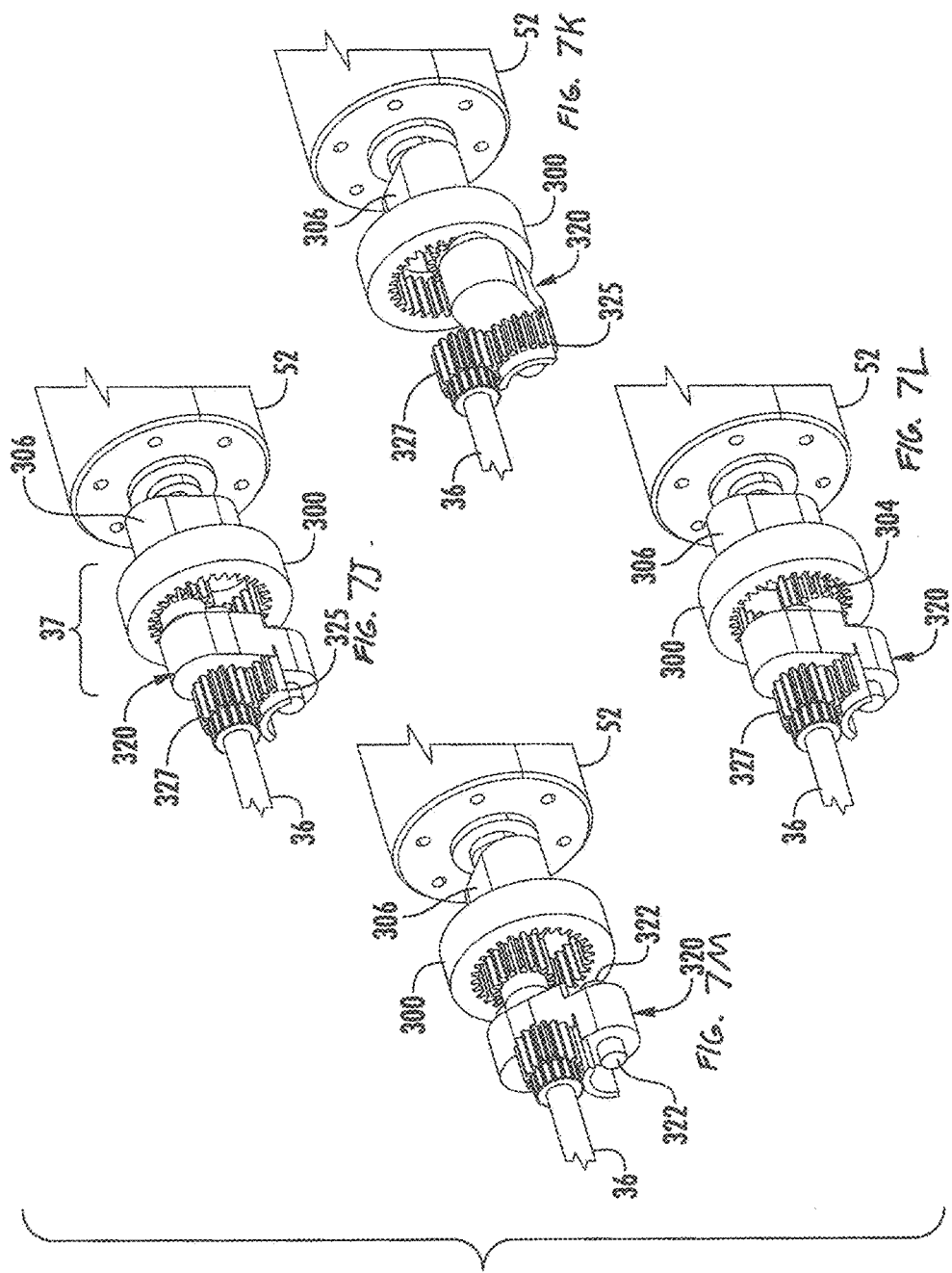

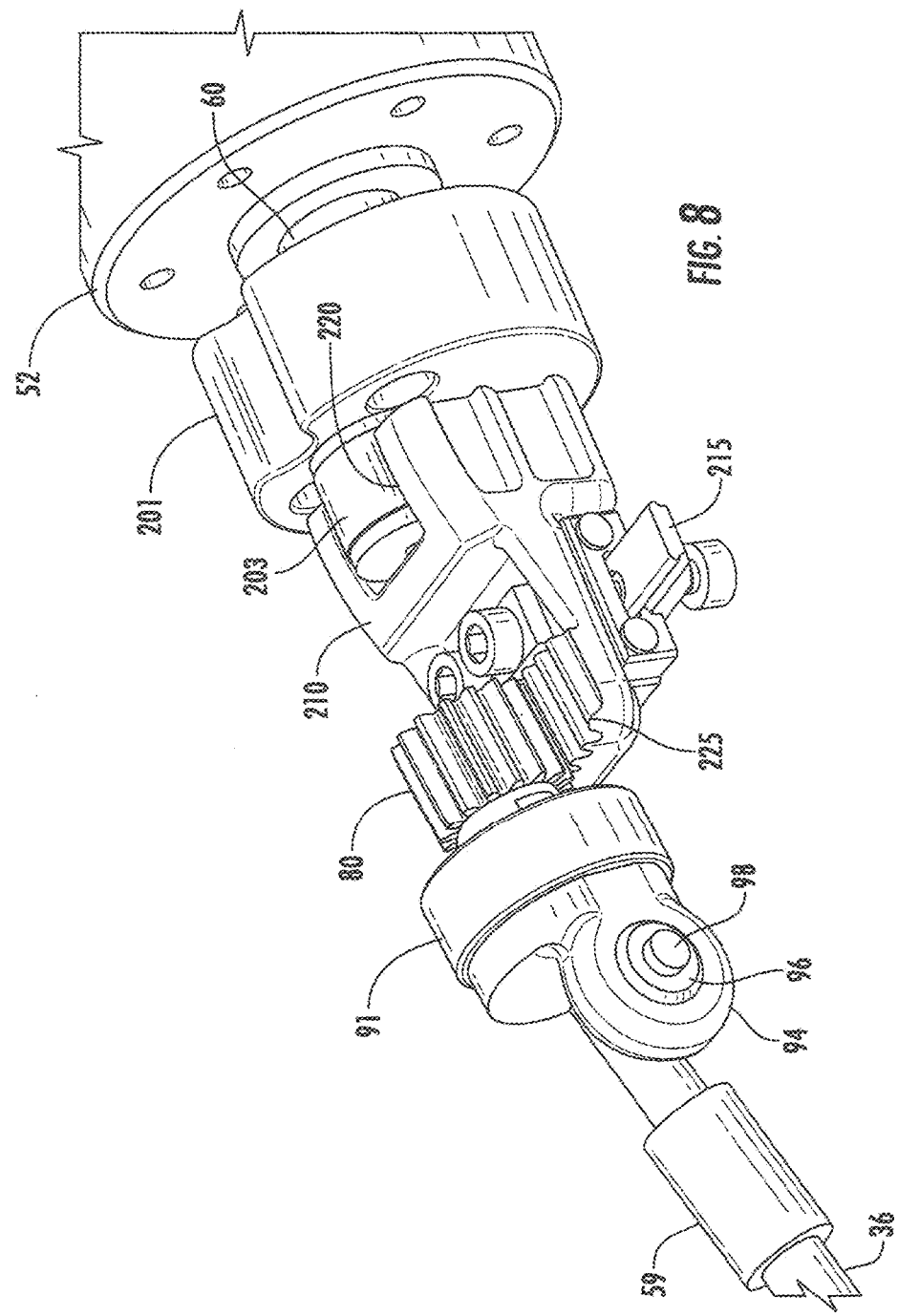

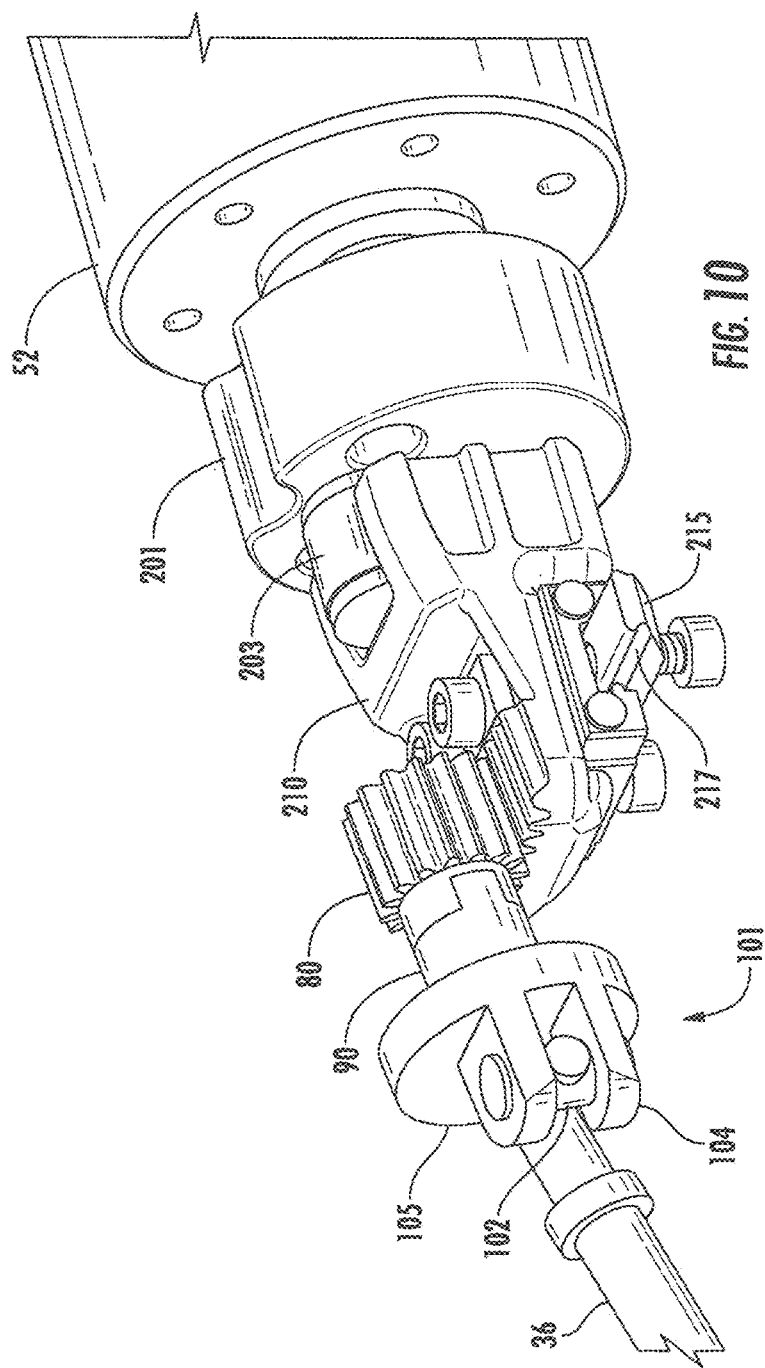

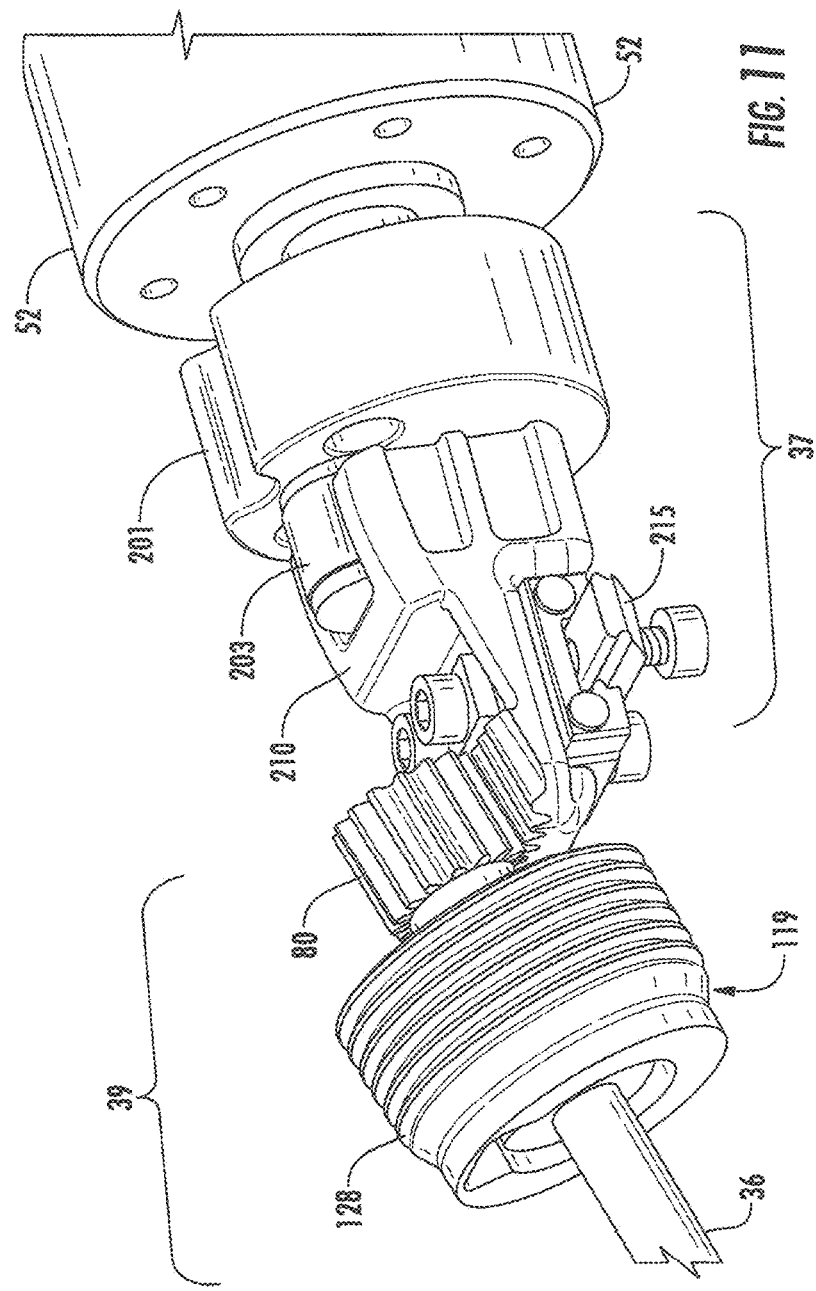

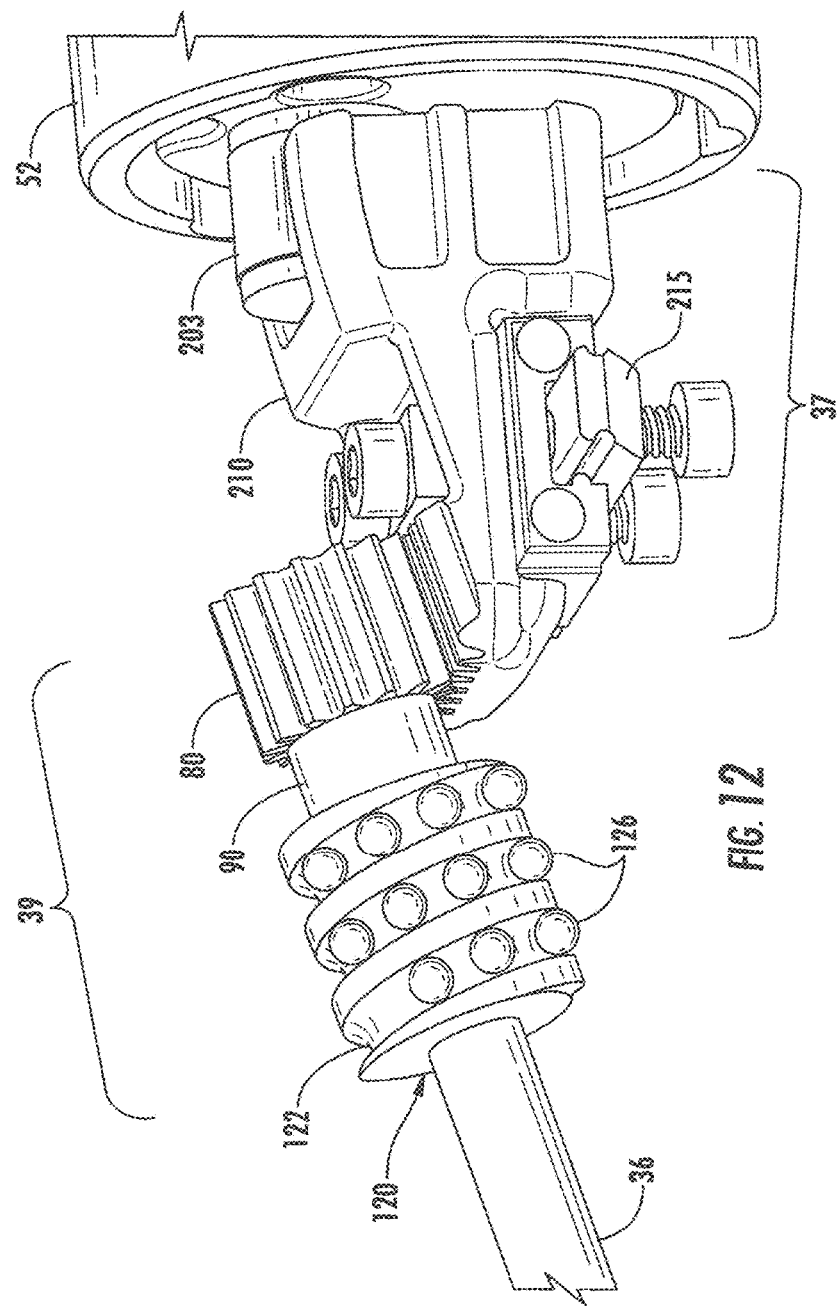

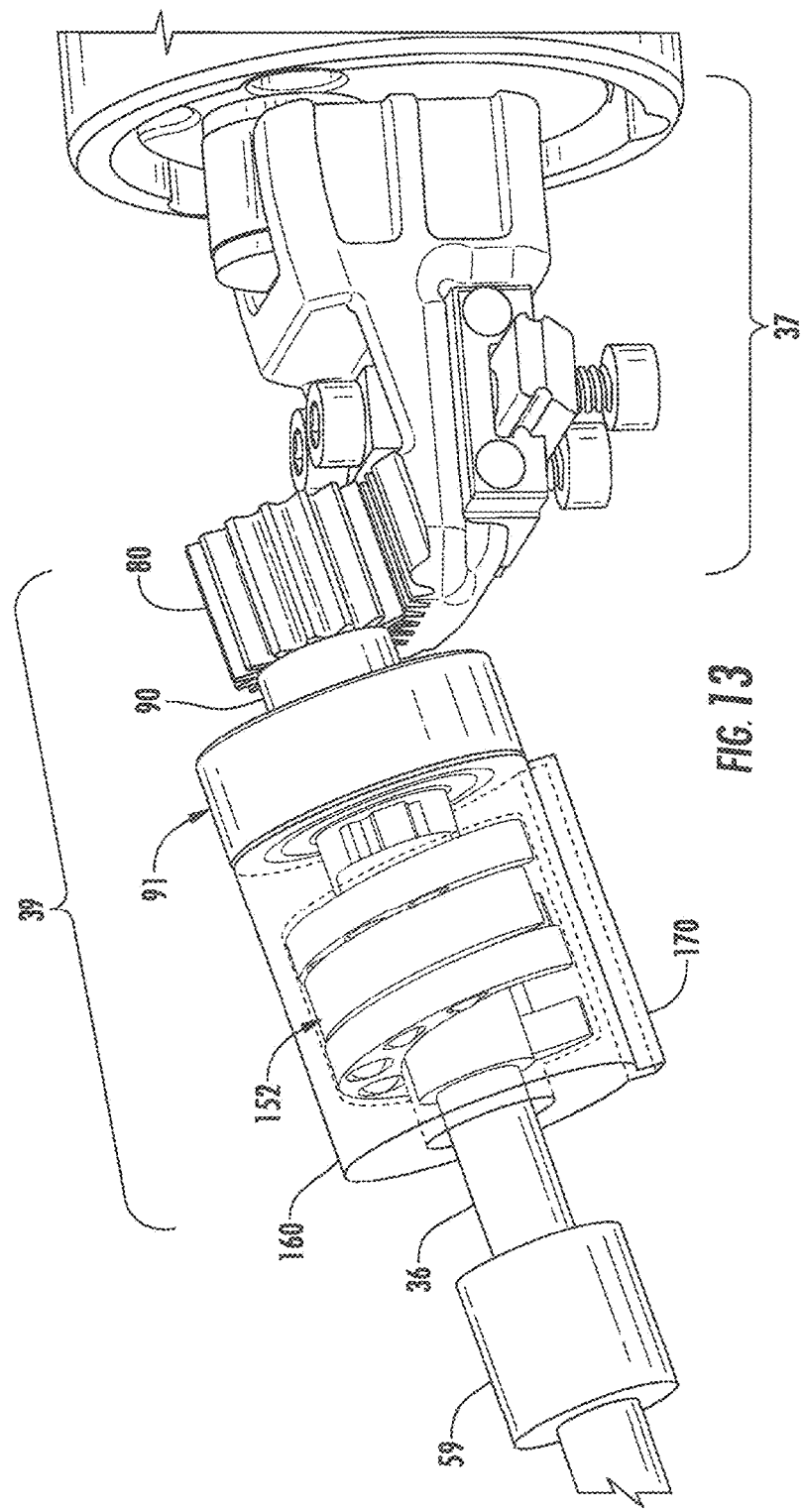

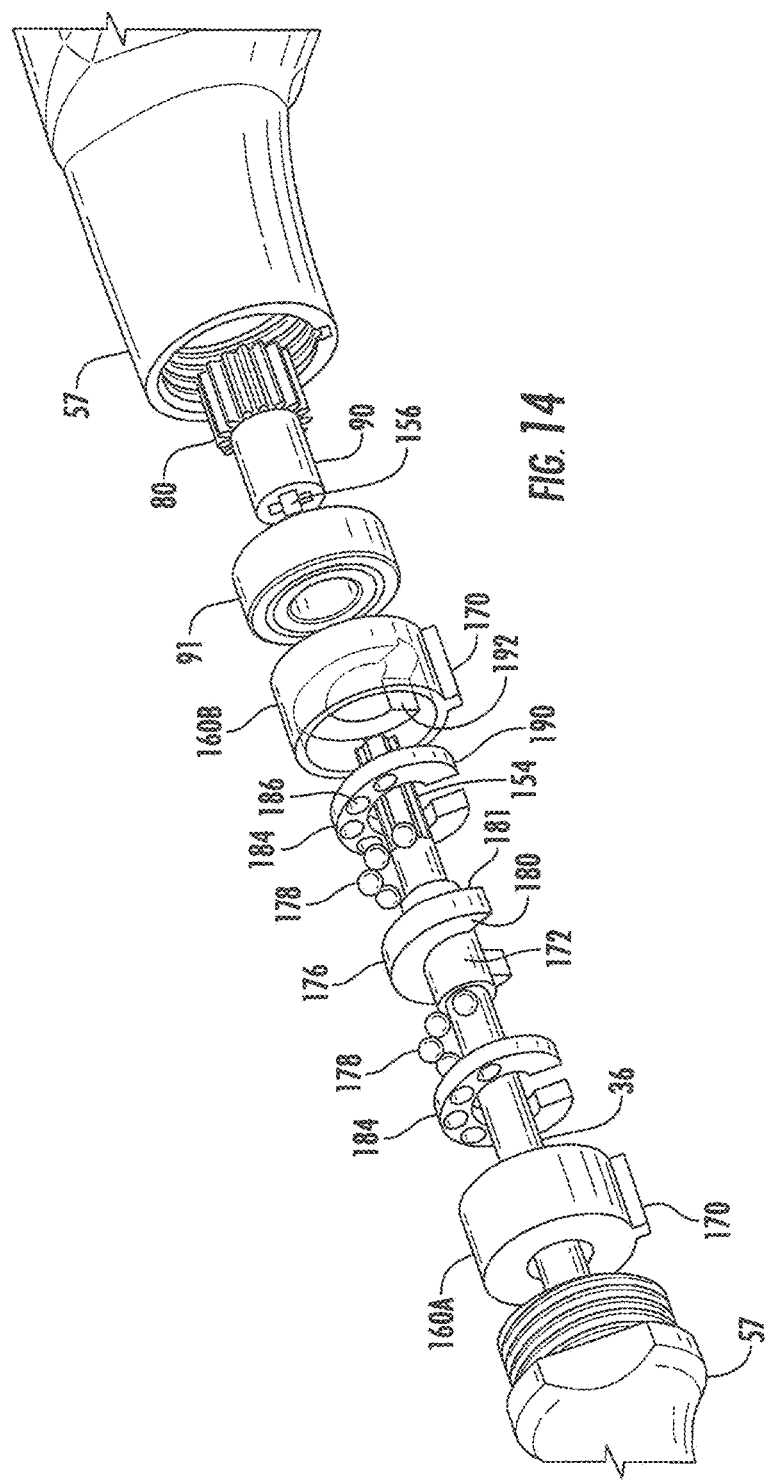

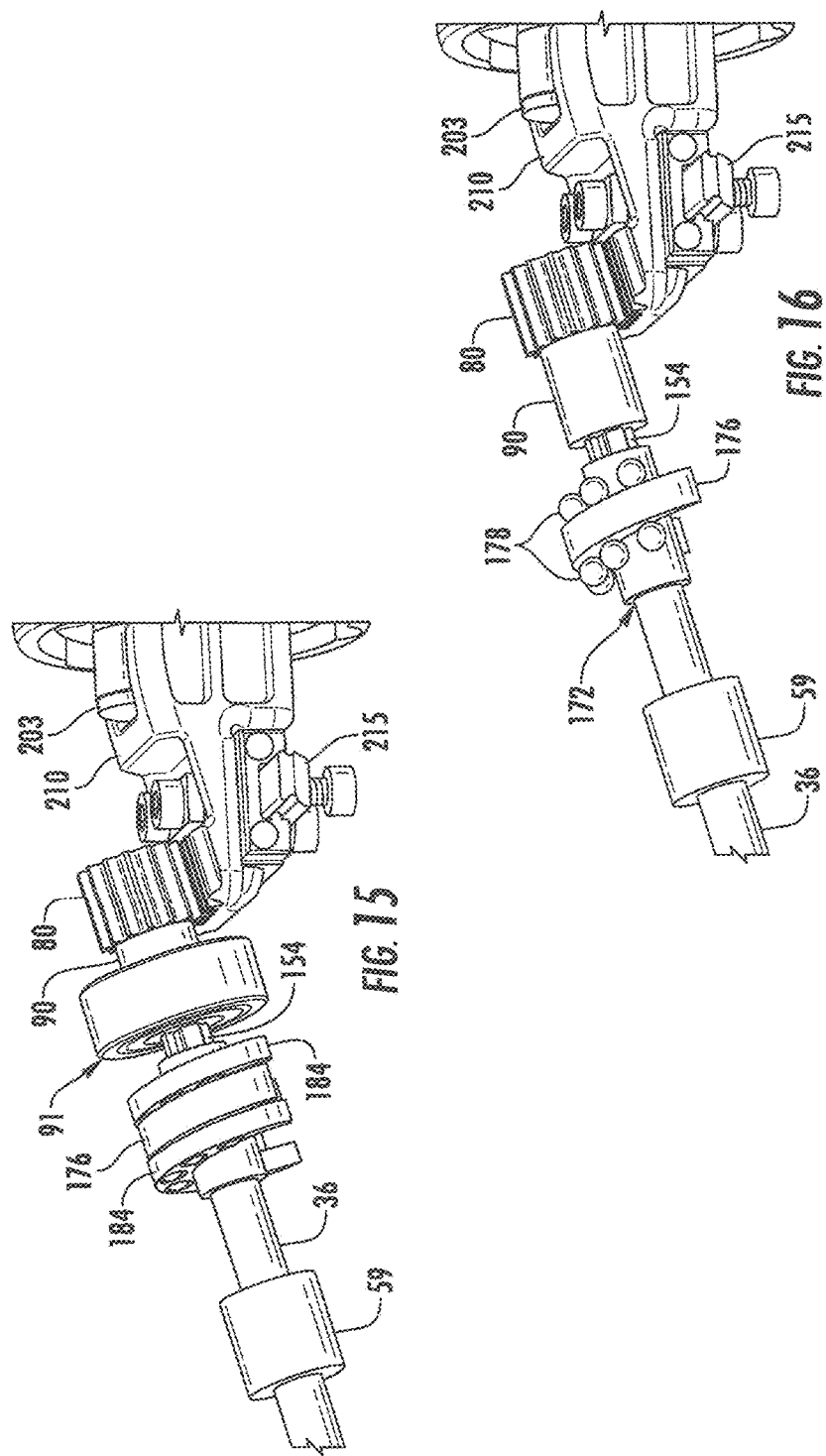

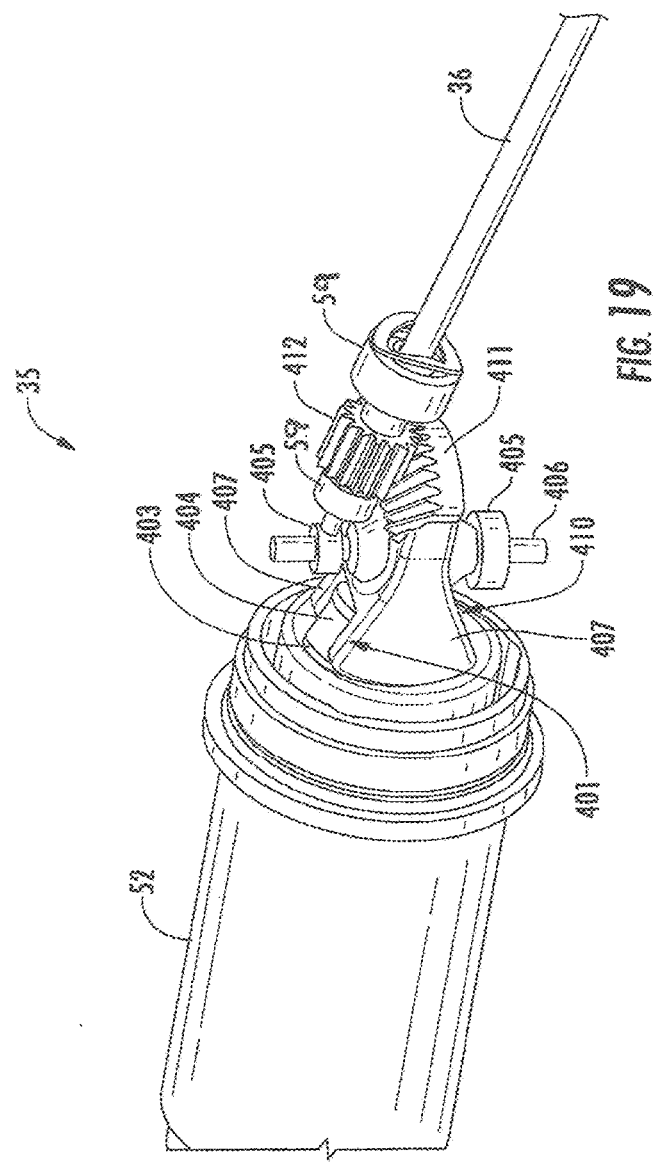

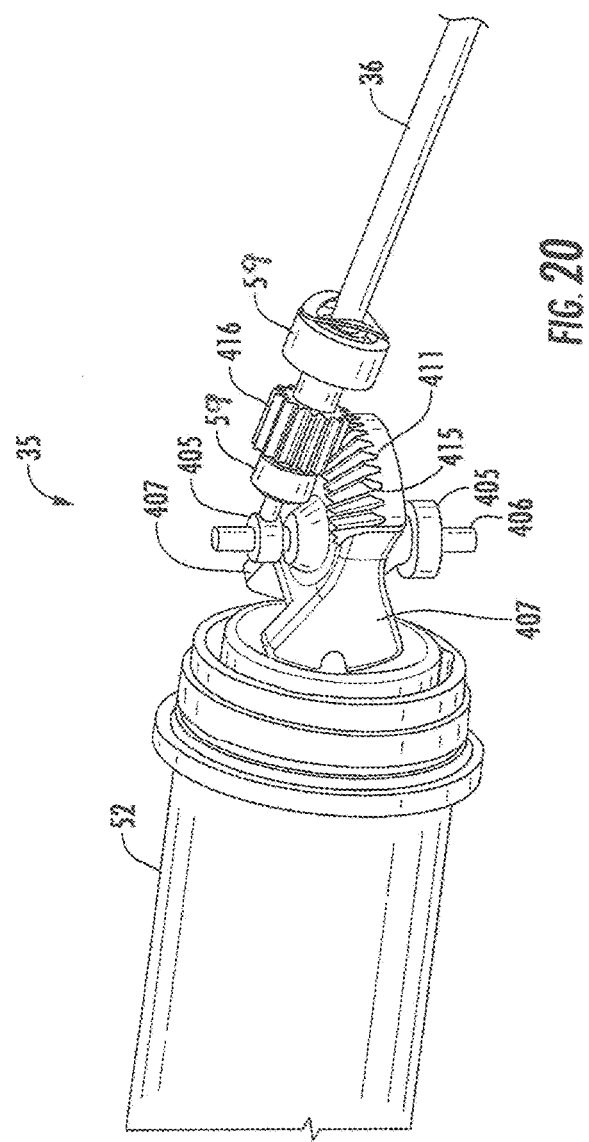

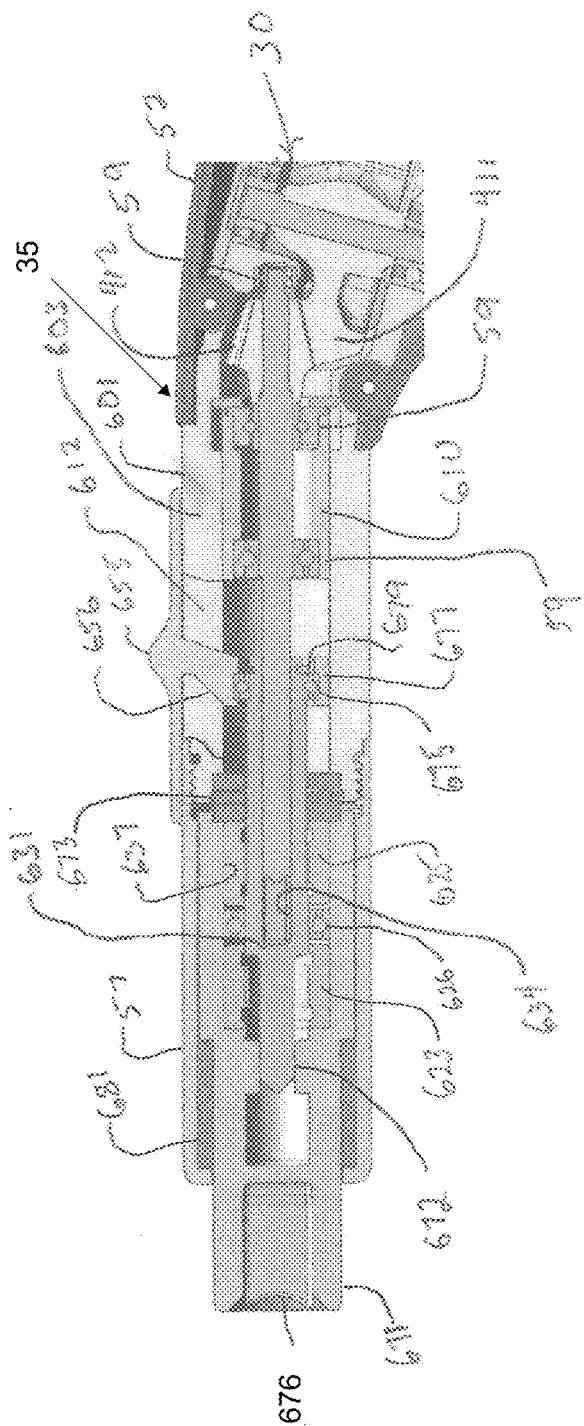

ROTARY OSCILLATING AND RECIPROCATING SURGICAL TOOL

CROSS REFERENCE TO RELATED APPLICATION

This application claims the benefit of U.S. provisional patent application Ser. No. 63/180,470 filed on Apr. 27, 2021, the disclosure of which is hereby incorporated herein by reference in its entirety.

FIELD OF THE DISCLOSURE

The present disclosure relates to a powered surgical tool with a cutter adapted to modify tissue such as bone, cartilage and discs. The tool can effect both rotary oscillation and longitudinal reciprocation of the cutter. The tool can also effect driving in a selected one of two rotational directions, as well as both rotational directions.

BACKGROUND OF THE DISCLOSURE

Currently there exists surgical tools having a rotary cutter adapted to modify tissue such as bone, cartilage and discs in a patient. Such tools, though, present a problem if the cutter encounters fibrous tissue, such as muscle and nerves. Such fibrous tissue can wrap around the cutter and be damaged thereby. Current systems also provided oscillating rotary tools for such surgical procedures, but the mechanisms used to effect oscillation of the cutter during its rotation do not operate smoothly due to the mechanisms used to effect oscillation. An advance in such oscillating tools is represented by co-pending applications: U.S. Non-Provisional patent application Ser. No. 13/469,665, entitled "Rotary Oscillating Bone, Cartilage, and Disk Removal Tool Assembly, filed May 11, 2012, which is now issued U.S. Pat. No. 10,194,922, issued on Feb. 5, 2019; U.S. International Application No. PCT/US2013/037071, entitled "Rotary Oscillating Bone, Cartilage, and Disk Removal Tool Assembly", filed Apr. 18, 2013; U.S. Non-Provisional patent application Ser. No. 13/647,101, entitled "Cutting Tool for Bone, Cartilage, and Disk Removal", filed Oct. 8, 2012, and now issued U.S. Pat. No. 9,232,953, issued on Jan. 12, 2016; U.S. International Application No. PCT/US2013/063182, entitled "Cutting Tool for Bone, Cartilage, and Disk Removal", filed Oct. 3, 2013; U.S. Provisional Patent Application No. 62/460,481, entitled "Surgical Rotary Tool", filed Feb. 17, 2017; U.S. Non-Provisional patent application Ser. No. 15/895,352, entitled "Surgical Rotary Tool", filed Feb. 13, 2018; U.S. Non-Provisional patent application Ser. No. 15/932,361, entitled "Surgical Rotary Tool", filed Feb. 16, 2018; U.S. Provisional Patent Application No. 62/423,624, entitled "Rotary Oscillating Surgical Tool", filed Nov. 17, 2016; U.S. Non-Provisional patent application Ser. No. 15/814,891, entitled "Rotary Oscillating Surgical Tool", filed Nov. 16, 2017; U.S. Provisional Patent Application No. 62/423,651, entitled "Robotic Surgical System", filed Nov. 17, 2016; U.S. Provisional Patent Application No. 62/423,677, entitled "Robotic Surgical System", filed Nov. 17, 2016; and U.S. Non-Provisional patent application Ser. No. 15/816,861, entitled "Robotic Surgical System", filed Nov. 17, 2017, and now issued U.S. Pat. No. 11,135,026, issued on Oct. 5, 2021. The contents of each of the above referenced applications are herein incorporated by reference.

Such tools are typically small and lightweight, with little room for drive mechanisms. They tend to operate at high cutting speeds for cutting efficiency and are controlled by a surgeon. Oscillations are on the order of at least about 10,000 oscillations per minute (5,000 orbits per minute), and may be 30,000-50,000 oscillations per minute or more. Reciprocation rate is preferably the same. An oscillation is movement of the cutter from one rotational position extreme to its other rotational extreme. Reciprocation is movement of the cutter from one linear movement position extreme to its other linear movement extreme. The cutter configuration and material being removed will determine cutter speed. Because of the high speed and need for precision placement and cutting, the tools need to be smooth in operation with little vibration.

Powered surgical tools for tissue removal are well known in the art as exemplified by the above referenced tools. Such tools typically are configured for operating in one of four modes. A first mode is to effect rotation of an end effector (e.g., a surgical tool such as a tissue cutter) in one direction of continuous rotation. A second mode is to effect oscillating rotation of an end effector in reversing directions of rotation. A third mode is to effect both rotation of the end effector, and simultaneously effect longitudinal reciprocating movement of the end effector. A fourth mode of operation is to effect only longitudinal reciprocating movement of the end effector.

While these tools are effective, they operate in only one mode of end effector movement. An additional tool is needed if the mode of operating needs to be changed, for example, tissue removal to install a screw fastener. There is thus a need for a multi operating mode powered surgical tool that can be used for both tissue removal and fastener installation.

SUMMARY OF THE DISCLOSURE

According to one embodiment of the present disclosure, a surgical tool is provided with a housing, a cutter (end effector) support shaft that is operably connected to a motor to effect oscillating rotation of the shaft, and a drive transmission configured between the motor and the shaft to effect oscillating rotary movement of the shaft and cutter mounted to the shaft.

It is an objective of the present disclosure to provide such a surgical tool that utilizes a second transmission coupled between the first transmission and an end effector that is operable to selectively effect oscillating rotation in at least one rotational direction.

It is yet another objective of the present disclosure to provide such a surgical tool wherein the second transmission is operable to selectively effect non-oscillating rotation in one of two rotational directions.

It is a still further objective of the present disclosure to provide such a surgical tool with means to removably mount an end effector to an output coupler to allow the selective use of different end effectors.

Other objects and advantages of this disclosure will become apparent from the following description taken in conjunction with any accompanying drawings wherein are set forth, by way of illustration and example, certain embodiments of this disclosure. Any drawings contained herein constitute a part of this specification, include exemplary embodiments of the present disclosure, and illustrate various objects and features thereof.

BRIEF DESCRIPTION OF THE FIGURES

FIG. 1 is a perspective view of the surgical tissue removal tool;

FIG. 2 is a cutaway fragmentary perspective view of the surgical tool of FIG. 1;

FIGS. 6A-6C illustrate various rotary positions of components of the second driver in the surgical tool that effect reciprocating movement of the cutting tool;

FIGS. 7A-7I illustrate a Cardan type first driver of the transmission;

FIGS. 7J-7M illustrate the Cardan drive of FIG. 7A, and also include the output of the first driver and the input of the second driver;

FIG. 8 is a fragmentary perspective view of one embodiment of a drive transmission;

FIG. 10 is a fragmentary perspective view of a drive transmission similar to that shown in FIG. 8;

FIG. 11 is a fragmentary perspective view of another embodiment of a drive transmission similar to that shown in FIG. 8, but with an alternate second driver;

FIG. 12 is a fragmentary perspective view of a drive transmission showing details of parts in FIG. 11;

FIG. 13 is a fragmentary perspective view of another embodiment of a drive transmission;

FIG. 14 is an exploded fragmentary perspective view of a portion of the drive transmission shown in FIG. 13;

FIG. 15 is a fragmentary perspective view of portions of the drive transmission of FIG. 13;

FIG. 16 is a fragmentary perspective view of portions of the drive transmission of FIG. 13;

FIG. 19 shows a fragmentary perspective view of another embodiment of a drive transmission with a drive rack in a first rotated position;

FIG. 20 shows a fragmentary perspective view of the drive transmission with a drive rack in a second rotated position;

FIGS. 23A-C are a series of sectional views showing different operational configurations of two transmissions that are operable to provide oscillating rotary motion selectively in one of two directions or two unidirectional directions of a surgical device.

DETAILED DESCRIPTION OF THE DISCLOSURE

Figure 3:
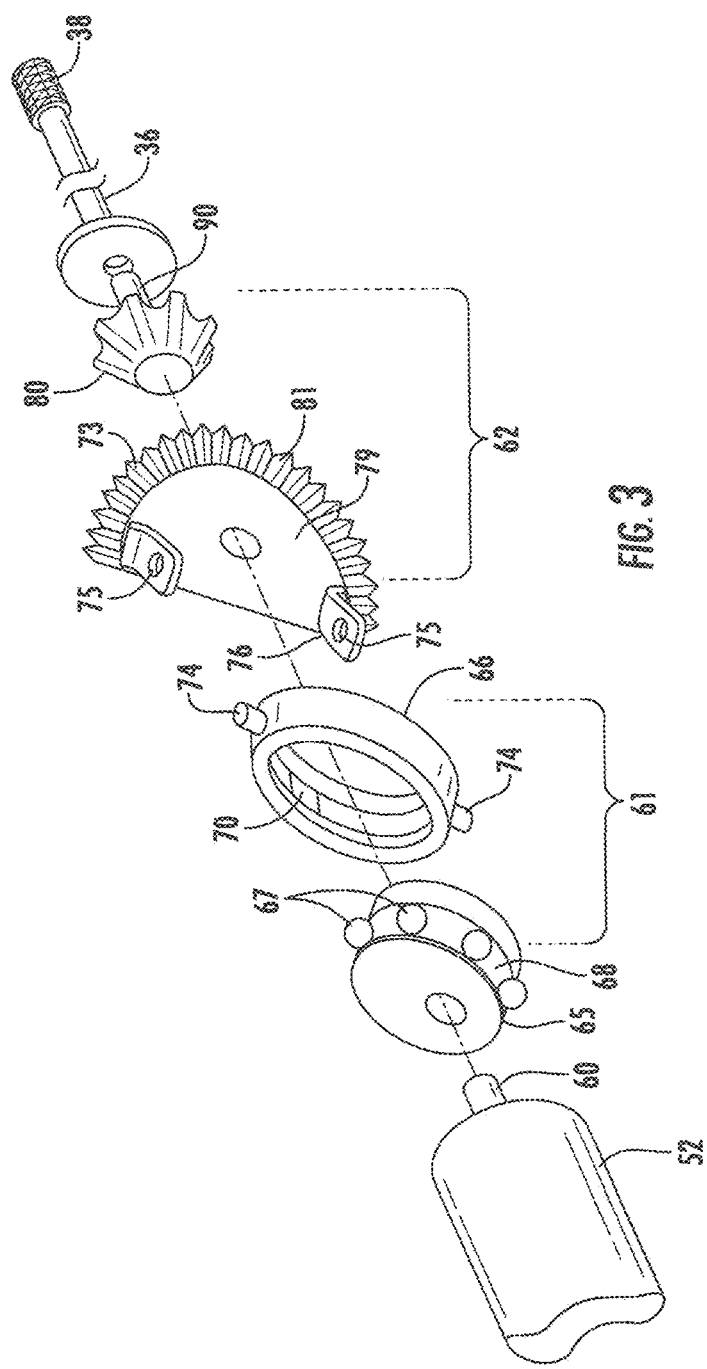
FIG. 3 is an exploded perspective view showing details of the internal parts of the surgical tool shown in FIG. 1.

The reference numeral 30 designates, generally, a rotary oscillating and reciprocating surgical tool useful, particularly, in the modification and/or removal of hard tissue, such as bone, cartilage and disc. The surgical tool 30 is a handheld tool with a housing 32 providing a handle 34 for manually gripping the tool 30 for use during a surgical procedure. While one shape and style of handle 34 is illustrated, any suitable shape and style of handle can be provided. For example, a right angle pistol grip may be added. Additionally, the housing 32 may have a narrow front portion for a smaller pencil-like "precision grip", while the larger remaining portion is sized to balance in the user's hand, such as in the web area between the index finger and thumb, for allowing better control with less fatigue.

The tool 30 can be used in surgical operations such as spinal surgery, wherein tissue such as bone, cartilage and disc material that is preferably of a non-fibrous tissue type may be modified or removed, such as from the spine of a patient. The tool 30 has an output shaft 36, which is driven to rotate in an oscillating manner of two alternate directions about the longitudinal axis of the shaft 36 by a first drive transmission 35 that can have two drive components, including an oscillation effecting first driver 37. Shaft 36 is provided with a surgical device 38, such as a cutting tool or driver bit, positioned and mounted to a distal end portion of the shaft 36. The cutting tool, or end effector, 38 is driven to rotate in alternate directions (oscillation) like the shaft 36, with a limited range of angular displacement of rotation, for example, between about 90° and about 180°. It has been found that such oscillatory rotation is effective in cutting or modifying hard tissue like bone, cartilage and portions of discs. It has also been found that this oscillatory rotation reduces the risk of damage to fibrous tissue, such as muscle and nerve. The tool 30 is provided with the first transmission 35 which includes the driver 37 to effect the oscillating rotation of the shaft 36 and its attached surgical device 38. The transmission 35 can be provided with a reciprocation effecting second driver 39 coupled to the first driver 37 to simultaneously effect reciprocating motion of the shaft 36 and surgical device 38 while they are oscillating in rotation. The second driver 39 uses the oscillating output of the first driver 37 to add the reciprocating motion to the shaft 36 and cutting tool 38. Reciprocating movement is parallel to the longitudinal axis of the shaft 36. The first driver 37 is upstream operationally of the second driver 39.

The tool 30 can receive energy for its operations from an external supply, such as a direct current power supply cord 40. A power control switch 42 can be provided on the housing 32 for controlling the operation of the tool 30, such as in an ON and OFF manner and/or in a variable speed manner. A light source 44 may also be provided on the housing 32 for illuminating the surgical site. Such a light source may be a light emitting diode (LED), which can be powered directly or indirectly by energy from the cord 40. Energy can also be provided by a battery 46 or other energy storage device. The battery can be rechargeable or non-rechargeable.

FIG. 2 illustrates internal components of the tool 30. An energy source can be provided by a battery supply 46 mounted in the housing 32. The battery supply 46, if rechargeable, can be charged by the power cord 40. Electronics 48 are provided in the housing 32 for controlling the operation of the tool 30. A plurality of indicator lamps 50 may also be provided on the housing 32 and can be LEDs for indicating operational characteristics of the tool 30, such as the state of charge of the battery supply 46. Alternately, the batteries 46 can be eliminated in favor of the cord 40 being connected to a source of electrical energy. Preferably, the power supply is low voltage, e.g., 12 volts. Additionally, the motor 52 can be powered by compressed air, a vacuum, or any other suitable source of energy that would, on demand, effect rotation of a rotor portion of the motor 52.

The motor 52 is suitably mounted in the housing 32, wherein a portion of the motor, a rotor (not shown), is free to rotate and ultimately drive the shaft 36. A portion of the motor 52 is fixed against rotation in the housing 32 as is known in the art; for example, a motor housing and/or stator. The motor 52 drives the shaft 36 through the first transmission 35 and its drivers 37, 39. The first driver 37 is operable for converting continuous rotary motion from the motor 52 to rotary oscillation of the shaft 36. The second driver 39, if included to provide reciprocating movement, is operable for converting continuous oscillation from the first driver 37 and continuous rotation of the motor 52, and adds continuous reciprocating longitudinal movement to the shaft 36. The shaft 36 is suitably mounted in the nose 57 of the housing 32, as in one or more bearings 59. Operationally, the first driver 37 is upstream of the second driver 39. The journal bearings 59 need to accommodate both rotary and linear movement (if the second driver 39 is utilized) of the shaft 36, and a suitable bearing is a journal bearing. The shaft 36 may be angled relative to the longitudinal axis of the housing 32, as depicted in FIG. 1, for ergonomics. Cooling fins, or a cooling fan, (not shown) may be attached to or near the motor 52 for cooling the motor and/or the tool 30.

FIGS. 3-18 illustrate different forms of drivers 37 and 39.

Figure 4:
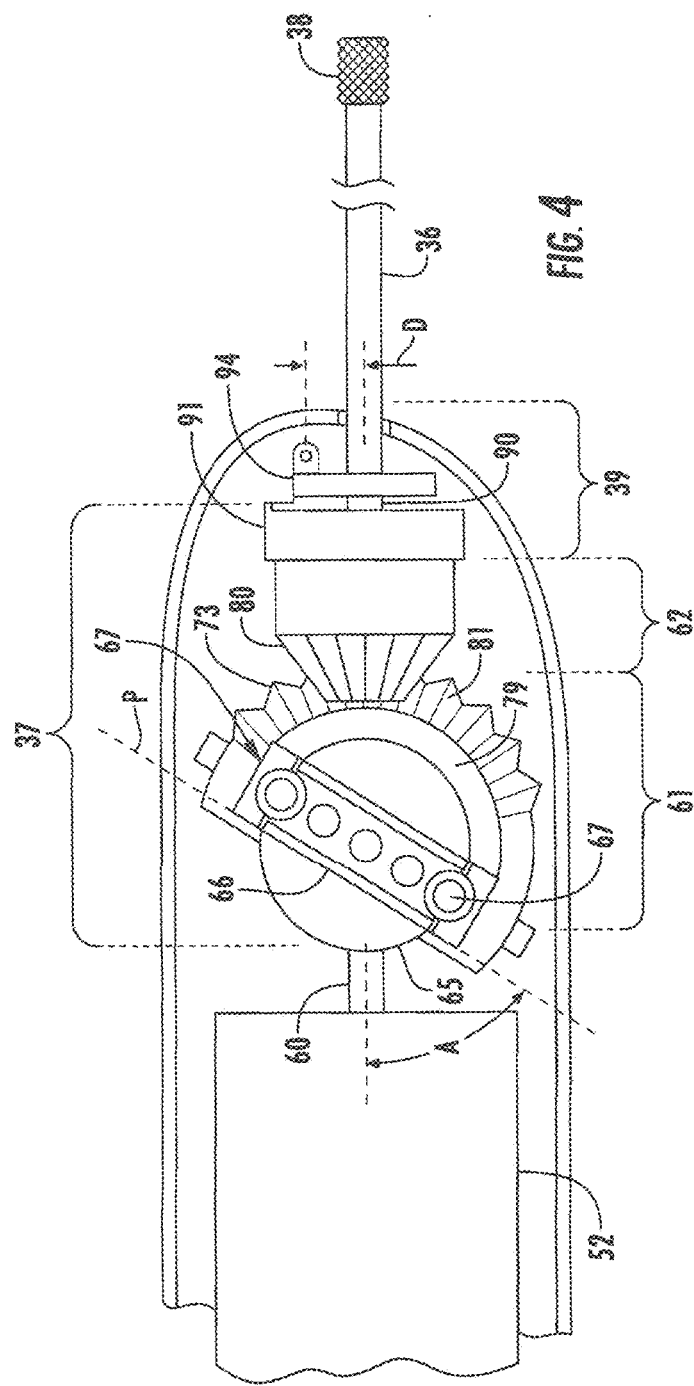
FIG. 4 is a top plan view of the details of the internal parts of the surgical tool shown in FIG. 1.
Figure 5:
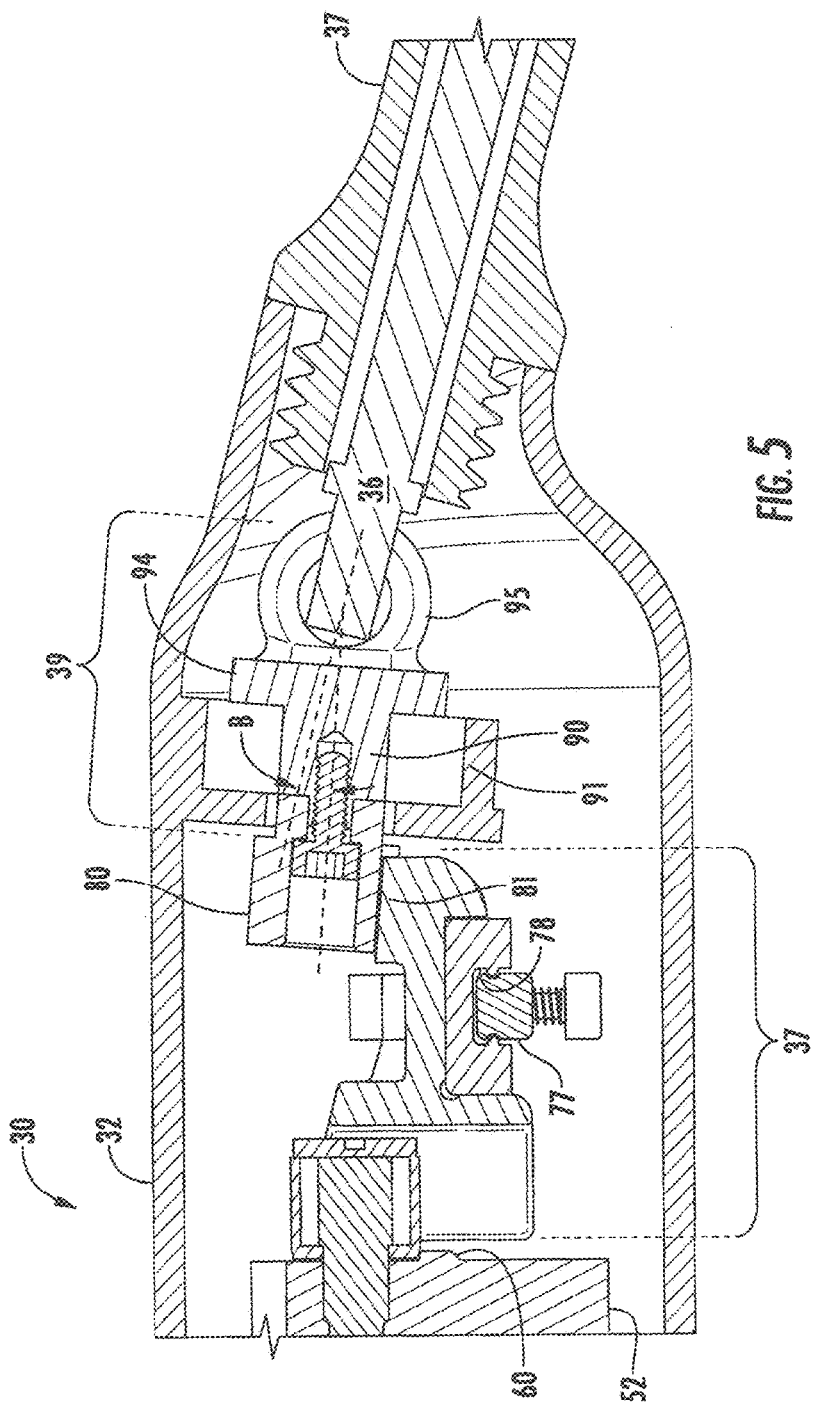
FIG. 5 is a fragmentary side view showing two drivers in the surgical tool shown in FIG. 1.

The first driver 37, as best seen in FIGS. 3-4, is positioned in the housing 32 and operably couples the second driver 39, and hence shaft 36, to the motor 52, and is operable to convert the continuous rotary motion of the shaft 60 of the motor 52 to oscillating rotary motion of the shaft 36. By oscillating rotary motion, it is meant that the shaft 36 will rotate a portion of a complete revolution first in one rotation direction and then in the other rotation direction, first counterclockwise, then clockwise, then counterclockwise again, and so on. To effect this movement, the transmission 35 comprises the two driver components 37, 39. The first driver 37 is operable to convert the rotary motion of the shaft 60 of the motor 52 to oscillating rotary motion of the shaft 36, and the second driver 39 is operable to convert that oscillating motion to reciprocating linear motion while maintaining the oscillating motion.

In the illustrated embodiment, the first transmission driver 37 includes a ball bearing having an inner race 65, an outer race 66 and a plurality of bearing balls 67 contained in the races 65, 66. The inner race 65 is secured to the motor shaft 60 for rotation thereby about the central axis of the motor shaft 60. In the illustrated embodiment, the inner race 65 is in the form of a sphere, with a groove 68 therein, and sized to receive and retain the balls 67 therein. The outer race 66 is in the form of a ring, having a groove 70 recessed in the inner surface thereof, and sized to receive and retain the balls 67 therein. The grooves 68, 70 open toward one another and are positioned in a plane P that is set at an angle A relative to the longitudinal axis of the motor shaft 60. The angle A is the smallest angle between the plane P and shaft axis since the angle of the plane P relative to the shaft axis changes depending on the position from which the measurement is taken. The angle A is in the range of between about 30° and about 80°.

The outer race 66 is coupled to an oscillating connector 73, as for example with a pair of opposed pivot pins 74 projecting outwardly from the outer race 66 and each being received in a respective bore 75 in a respective boss 76. The connector 73 is restrained in movement to a plane. In one example, a guide 77 (FIG. 5) is secured to the housing 32. The guide 77 is curved, and is received in a similarly curved slot 78 cooperating with the driver 37. Thus, the outer race 66 can only move in an oscillating manner, as can the connector 73. Another means to mount the connector 73 is with a pivot pin secured to the housing 32 and extending through a web portion 79 of the connector 73, which allows the connector 73 to rotate in an oscillating manner. The illustrated connector 73 has a curved gear rack portion 81, preferably a sector gear, coupled to the web 79 and carried thereby. A gear or gear segment, herein a gear 80, such as a bevel gear, engages the rack portion 81 of the driver 37 and itself is driven in an oscillating manner by rotation of the inner race 65 as driven by the motor 52. The gear 80 is coupled to the shaft 36 by the second driver 39 to effect driving of the shaft 36 in an oscillating manner.

The angle A determines the degree of rotation of the gear 80, and the rotational speed of the motor 52 determines the oscillation rate of the gear 80.

Figure 6A:
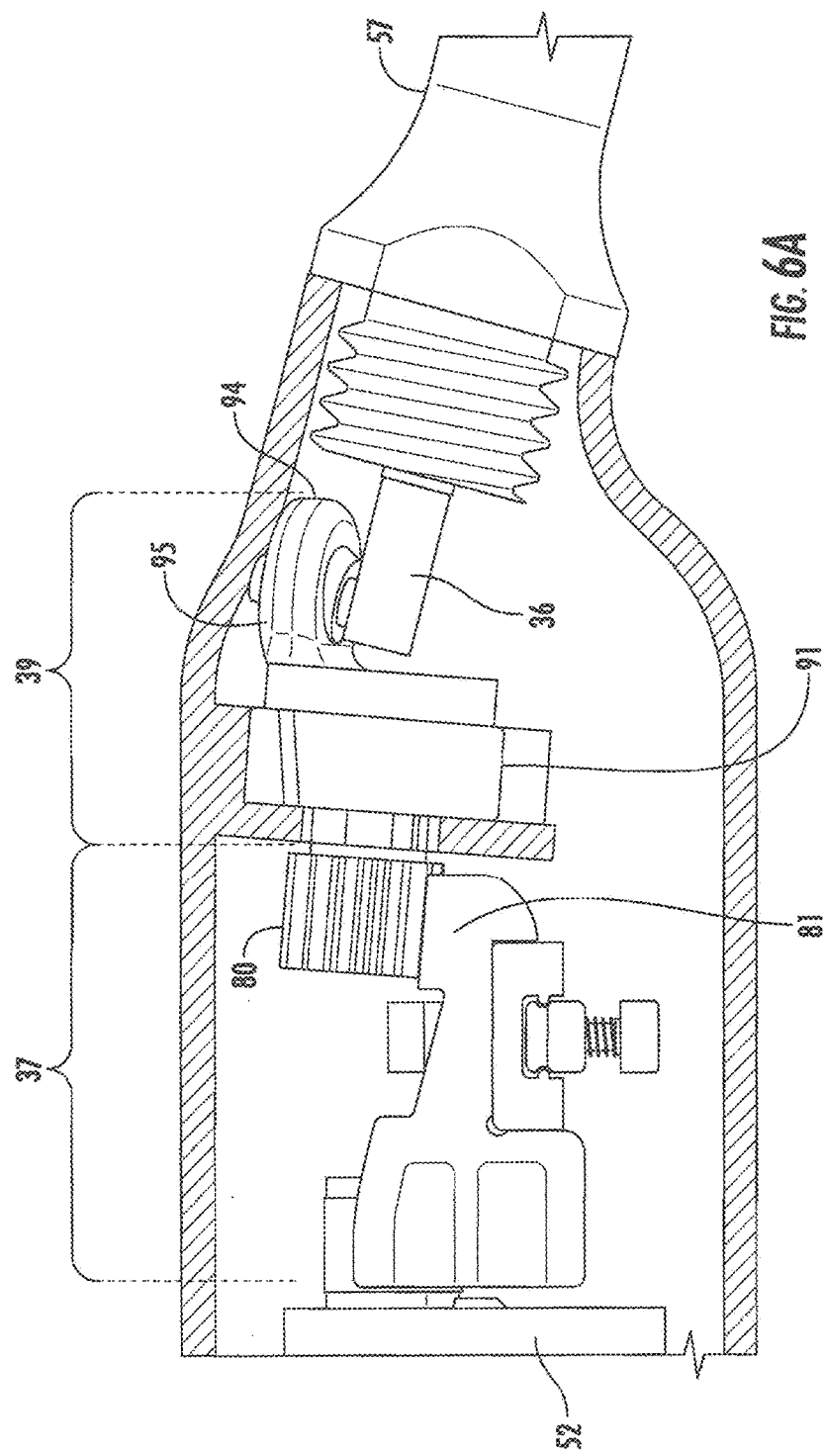

The gear 80 is part of the second driver 39, and is coupled to the shaft 36 to effect motion of the shaft 36 and associated cutting tool 38 as described herein. As shown, the gear 80 is fixed to a shaft 90 that is rotatably mounted to the housing 32 via a suitable bearing 91 fixed in position in the housing 32. The gear 80 is maintained in driving engagement with the rack 81, which oscillates along a curved path during operation of the motor 52. The shaft 36 is secured to a reciprocation effecting joint 94 in a manner allowing part of the joint 94 to pivot during rotation of the joint 94 and shaft 36. See FIGS. 6A-6C. Oscillation of the shaft 90 and the joint 94 effects oscillation of the shaft 36. The longitudinal axis of the shaft 90 intersects the longitudinal axis of the shaft 36, FIGS. 4, 5, and the axes are positioned at an angle B relative to one another. By being positioned at an angle B, which is preferably in the range of between about 5° and about 45°, the shaft 36, during oscillating rotation, will move longitudinally in two directions, effecting reciprocal movement of the shaft 36 and cutting tool 38 during their oscillating movement. To allow for both oscillation and reciprocation, the shaft 36 can be mounted in one or more journal bearings 59 fixed in position in the housing 32 and/or nose 57. The joint 94 acts as a wobble plate because of the angle B. Additionally, to effect the reciprocating movement, the shaft 36 is secured to the joint 94 at a position offset radially outwardly from the center of its rotation, the center of the shaft 90, FIGS. 4, 6A. This offset dimension D also determines the amount of reciprocating movement of the shaft 36. In a preferred embodiment, the joint 94 oscillates about 180° and starts at a rotational position, where the shaft 36 is at its most retractable position and ends at its most extendable position. The joint 94, as shown, includes a tab 95 on which is mounted a ball or spherical bearing 96. The shaft 36 is coupled to the bearing 96 as with a pin 98, FIG. 8. FIGS. 6A-6C illustrate the joint 94 in three different rotary positions and three different reciprocating positions. In FIG. 6A, the shaft is in its most extended reciprocating position. FIG. 6B shows the shaft 36 in an intermediate extended position. FIG. 6C shows the shaft 36 in its most retracted reciprocating position.

FIG. 10 illustrates another embodiment of connecting the shaft 36 to the second driver 39. The reciprocating effecting joint 101 is used instead of the joint 94. A pivot pin 102 is mounted for rotation in a clevis 104, which in turn is mounted to a crank member 105. The crank member 105 is mounted to a shaft 90, which is rotatably mounted in the bearing 91 as described above. The shaft 36 is secured to the pivot pin 102. This form of joint 101 is similar in operation to the joint 94 as described above.

FIGS. 11, 12 illustrate another embodiment of a second driver 39 that is operable to effect longitudinal reciprocating movement of the shaft 36. The shaft 36 is coupled to the shaft 90 relative to longitudinal movement therebetween, as for example, by the use of a spline connection, as can be seen in FIG. 14. An inner bearing race 120 is secured to the shaft 36 and has an outwardly opening helical bearing groove 122. A plurality of bearing balls 126 are contained within the groove 122. An outer bearing race 128 is mounted in the housing 32 or nose 57 and is fixed against movement relative thereto. The outer bearing race 128 has a helical groove (not shown) that opens inwardly and contains the bearing balls 126 therein. When the shaft 36 rotates in an oscillating manner, as effected by the first driver 37, the shaft 36 will move in a longitudinal reciprocating manner by cooperation between the inner and outer bearing races 120, 128, respectively, via the bearing balls 126. This forces the inner race 120 to move longitudinally in a reciprocating manner.

FIGS. 13-16 illustrate a further embodiment of a second driver 39 that is operable to effect longitudinal reciprocating movement of the shaft 36. This embodiment uses a helical bearing 152 to effect longitudinal reciprocating movement of the shaft 36 while the shaft 36 is being rotationally oscillated by the first driver 37. As seen in FIG. 14, the shaft 36 has its proximal end 154 male splined and is longitudinally movably received in a female splined socket 156 within the shaft 90. Thus, the shaft 36 can move both longitudinally and rotationally while being driven by the drivers 37, 39. The helical bearing 152 includes a split housing 160 having housing portions 160A and 160B. The housing 160 is mounted in the housing 32 and/or its nose 57 in a manner to prevent relative rotation therebetween. This can be accomplished, as seen in FIGS. 13, 14, by providing the housing 160 with a laterally projecting key 170. The bearing 152 has an inner race 172 secured to the shaft 36 and provides a radially projecting helically longitudinally extending flange 176. Bearing balls 178 are positioned on opposite faces 180, 181 of the flange 176. The helical bearing 152 is provided with a pair of outer races 184 that have a plurality of bearing ball receiving pockets 186 in the faces opposite the faces 180, 181. The outer races 184 retain the bearing balls 178 in contact with their respective face 180 or 181. Rotation of the outer races 184 relative to the housing portions 160A and 160B is limited by stop faces 190 on the outer races 184, and stop faces 192 on the inside of the housing portions 160A and 160B.

Figure 9:
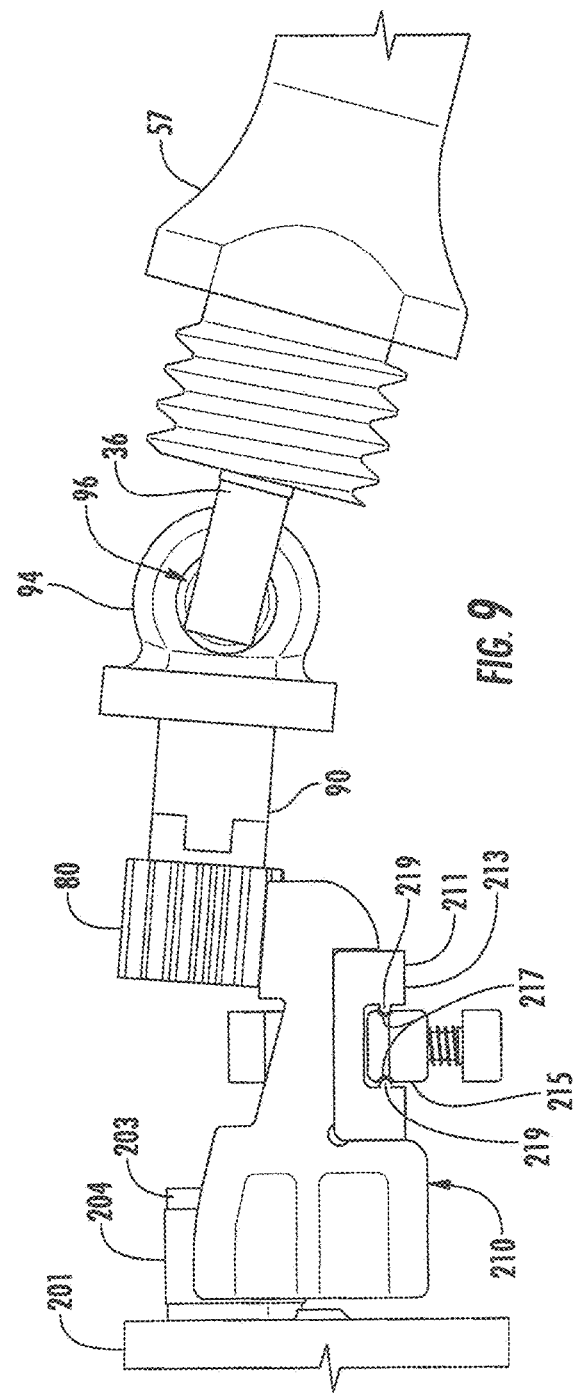
FIG. 9 is a fragmentary side elevation view of a drive transmission as seen in FIG. 5.
Figure 17:
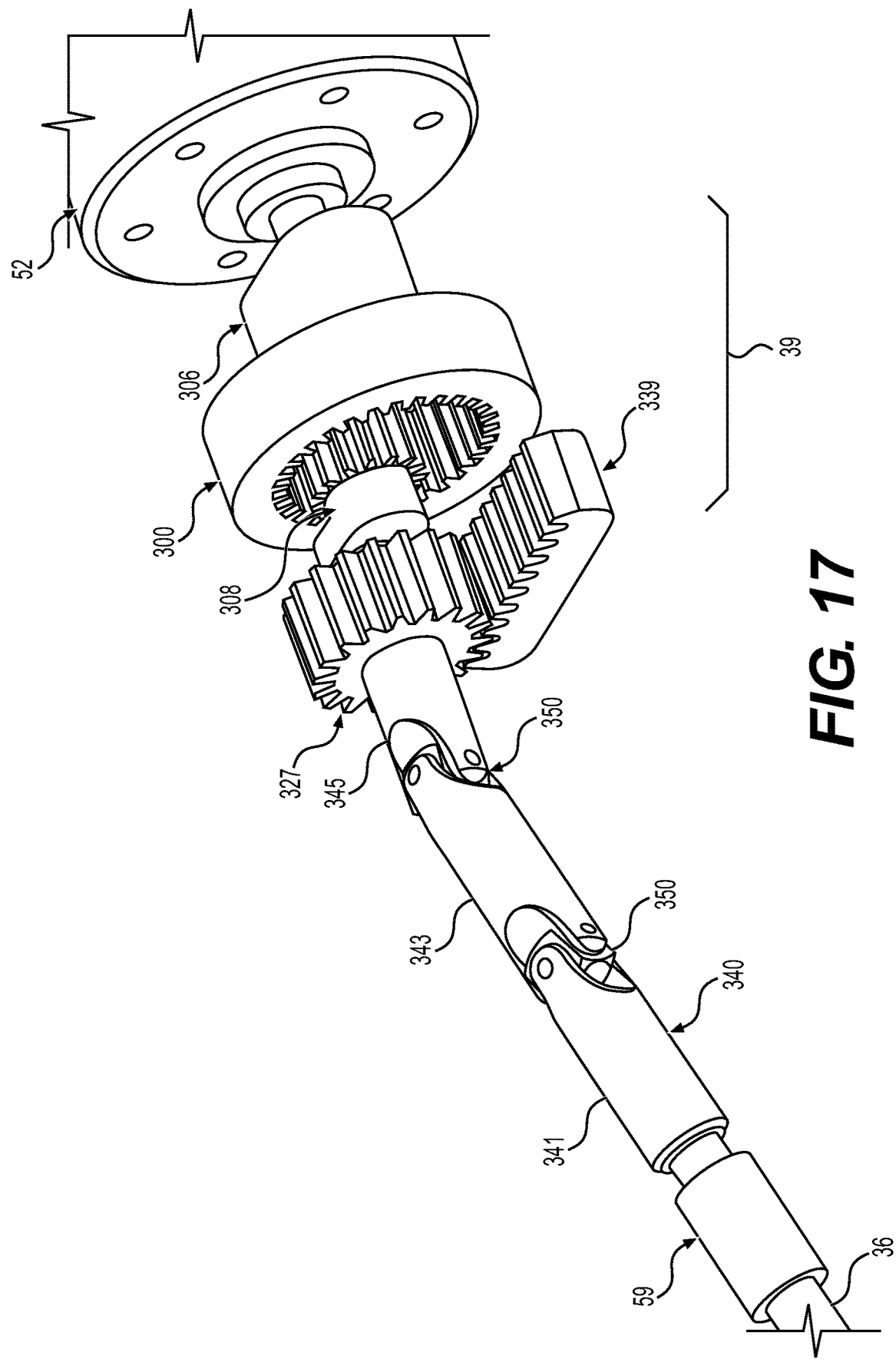
FIG. 17 is a fragmentary perspective view of portions of a still further embodiment of a drive transmission.
Figure 18A:
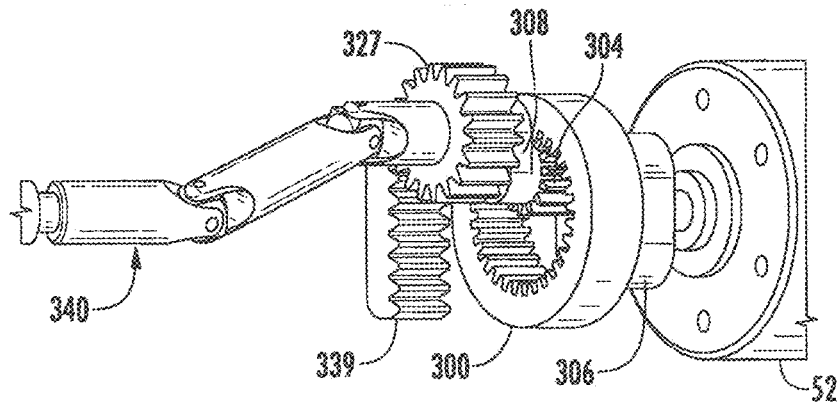
FIGS. 18A-18D are fragmentary perspective views of portions of the transmission of FIG. 17 showing sequential positions of portions of the second drive effecting reciprocating movement of a cutter shaft and associated cutter.
Figure 18B:
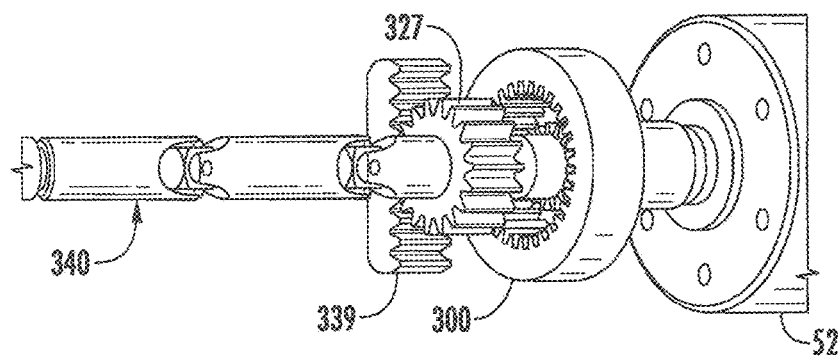
Figure 18C:
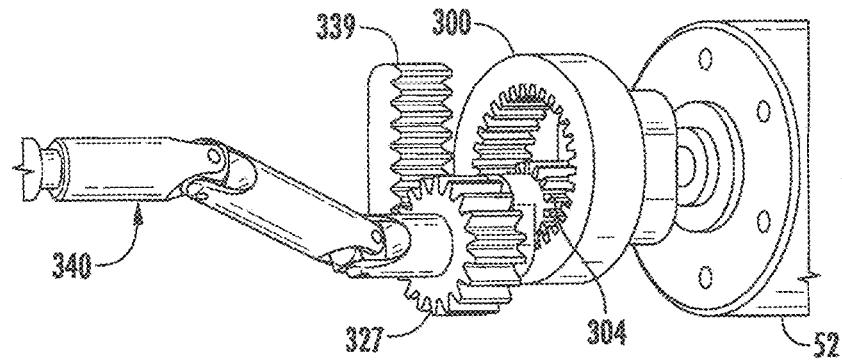
Figure 18D:
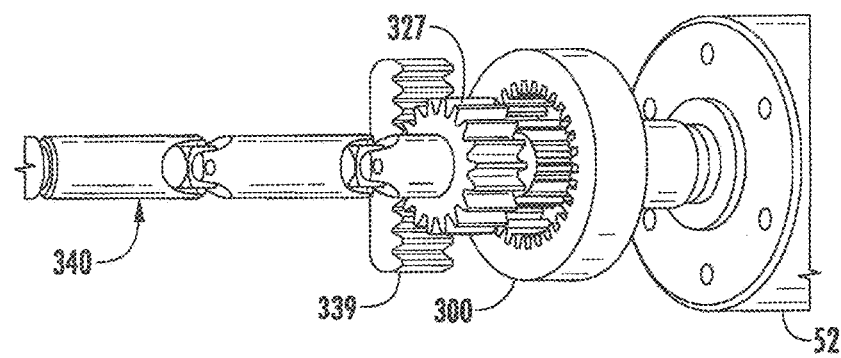

FIGS. 8, 9 illustrate a second embodiment of the first driver 37. It is similar to the driver 37 shown in FIGS. 5, 6A-6C. The motor 52 has a crank assembly 201 mounted on its output shaft 60. The crank assembly 201 includes a drive arm 203 that can include a wear resistant bearing member 204. The drive arm 203 is offset radially from the center of rotation of the crank assembly 201. Thus, rotation of the crank assembly 201 moves the drive arm 203 in a circular path. A follower assembly 210 is mounted in the housing 32 in a manner to restrict its movement in a plane laterally from side to side. As shown, a guide bed 211 is provided and includes a guide channel 213, which receives in it a guide rail 215. As shown, the guide rail 215 is coupled to the bed 211 to prevent their separation during movement. As illustrated, the guide rail 215 has a pair of opposed grooves 217, in each of which is received a respective guide rail 219 to provide guided restrained movement between the guide bed 211 and guide rail 215. The guide rail 215 is straight, thereby restricting movement of the follower assembly to linear movement in a plane. The drive arm 203 is received in a channel 220 with a close fit, whereupon revolving movement of the drive arm 203 will effect reciprocating lateral movement of the follower assembly 210. The follower assembly 120 is drivingly coupled to the second driver 39 in a manner to effect oscillating rotation of the shaft 36. As shown, a gear rack 225 is provided on the follower assembly 210 to mesh with the gear 80, whereby lateral movement of the follower assembly 210 effects oscillating rotation of the shaft 36, which, with operation of the second driver 39, will simultaneously effect reciprocating motion of the shaft 36.

FIGS. 7A-7M illustrate another form of drivers 37, 39. The first driver 37 is illustrated as a Cardan type drive that is operable to effect rotary oscillation of the shaft 36. While the structure shown in these Figures effects only oscillating rotation, the additional structure shown in FIGS. 17, 18A-18D shows a mechanism to convert the oscillating rotation into oscillating rotation and linear reciprocation of the shaft 36.

FIGS. 7A-7I illustrates the basic functioning of a Cardan mechanism. An internal gear member 300 has an external gear 304 received therein. The gear ratio between the internal gear 300 and the external gear 304 is 2:1. The gear 300, in this case, is fixed against movement, while the gear 304 is part of a crank arm 306 mounted to the motor 52. As the crank arm 306 effects revolving of the gear 304 about the center of rotation of the motor shaft, the gear 304 moves about the interior of the internal gear 300. The gear 304 has secured thereto an output arm 308 that has a center of rotation that is coaxial with the center of rotation of the motor 52 when the arm 308 is at its center position within the gear 300, as seen in FIG. 7B-7I. In this type of mechanism, the center of the arm 308 moves in a linear path in a laterally reciprocating manner. Thus, rotary output motion of the motor shaft can be converted into reciprocating linear motion. This can be seen in FIG. 17.

As seen in FIGS. 7J-7M, the Cardan style first driver 37 is coupled to a follower 320 that is operable to convert the linear movement of the arm 308 into oscillating rotary motion of the shaft 36. The illustrated follower 320 receives the arm 308 in an elongate slot (not shown) on the side facing the motor 52; this allows the arm 308 to move freely as the follower 320 pivots about a pair of pivot pins 322 that are mounted in suitable bearings (not shown) in the housing 32 and/or its nose 57. As the arm 308 moves laterally, as seen in FIG. 7A, it will force the follower 320 to pivot. A curved gear rack 325 secured to the follower 320, is preferably integral therewith, and has the gear teeth spaced radially outwardly from the pivot pins 322. The radius of the gear rack 325 is substantially the radial distance of the gears from the center of rotation of the pivot pins 322. The gear rack 325 is meshed with a gear or gear segment 327, such as a spur gear, that is secured to the shaft 36. As the follower 320 oscillates about its pivot pins 322, the shaft 36 is driven in a rotary oscillating manner.

FIGS. 17 and 18A-18D illustrate a still further embodiment of a second driver 39. It utilizes a Cardan first driver 37, such as shown in FIGS. 7J-7M. However, instead of a curved gear rack 325, this form uses a straight gear rack 339, and the gear 327 which is coupled to the shaft 36 moves laterally with its center of rotation being in a straight line. This can be accomplished by having the arm 308 centered on the center of rotation of the gear 304. The gear 327 is coupled to the shaft 36 through the use of a drive shaft 340. As shown, the drive shaft 340 has three sections 341, 343, and 345. Section 341 is secured to the shaft 36, which, in turn, is mounted in the bearing 59, as described above. Section 343 is coupled to section 341 in a manner that allows the axes of sections 341 and 343 to change their angular orientation. This can be accomplished by a universal joint (u-joint) 350. Section 343 is coupled to section 345 in a similar manner, as with a second universal joint 350. As the gear 327 rotates and moves laterally side-by-side on the gear rack 339, the length of the drive shaft 340 increases and decreases, effecting linear reciprocating movement of the shaft 36. This can be seen in FIGS. 18A-18D.

Figure 21:
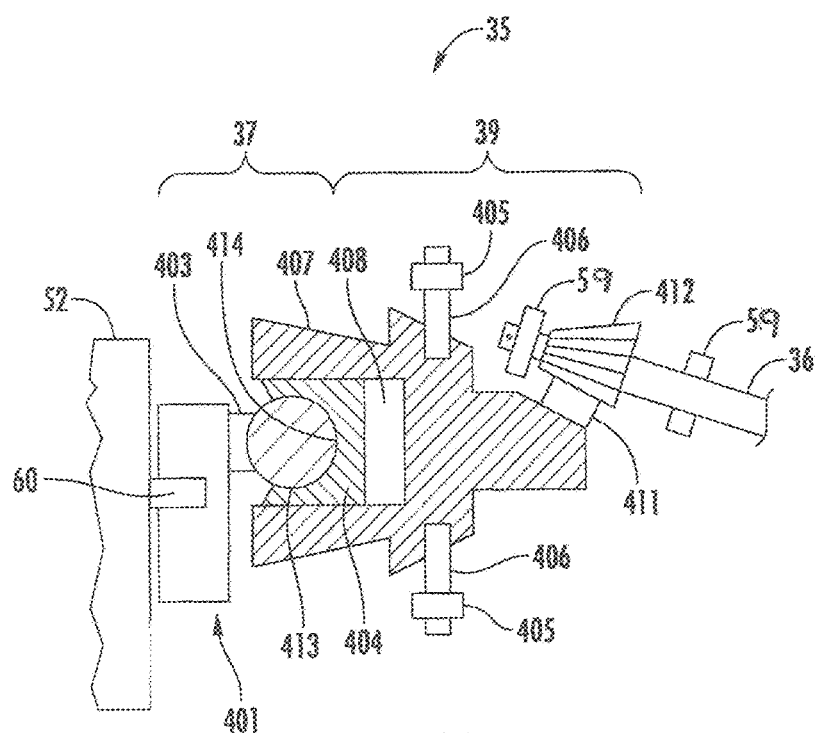
FIG. 21 is a side elevation view of the drive transmission of FIGS. 19, 20 with sections broken away to show details thereof.

FIGS. 19-21 illustrate another embodiment of the first transmission 35, first driver 37 and second driver 39. The transmission 35 in FIGS. 19-21 is similar to that shown in FIGS. 5, 6A-6C, in that it uses both a rack and pinion gear drive arrangement and a crank assembly. The motor 52, described above, has a crank assembly 401 mounted on its output shaft 60. The crank assembly 401 includes a drive arm 403 that can include a wear resistant bearing member 404. The drive arm 403 is offset radially from the center of rotation of the crank assembly 401. Thus, rotation of the crank assembly 401 moves the drive arm 403 in a circular path. A follower assembly 410 is mounted in the housing 32 in a manner to restrict its movement in a plane laterally from side to side in a pivoting manner about an axle arrangement 406. The axle arrangement 406 is mounted for pivoting movement of follower assembly 410 with suitable bearings 405 mounted in the housing 32. The follower assembly 410 has a pair of spaced apart arms 407, each with an inwardly opening channel 408 sized and shaped to receive the bearing member 404 therein. The channels 408 are portions of a cylinder and the bearing 404 is a cylinder, allowing the bearing 404 to move both longitudinally and rotationally relative to the follower assembly 410. The bearing 404 is mounted to the drive arm 403 in a manner to allow the drive arm to be rotated by the motor 52 and effect rotational pivoting movement of the follower assembly 410. As shown, the drive arm 403 is provided with a generally spherical bearing 413 mounted in a spherical cavity 414 in the bearing 404 that permits multi axis rotation of the bearing 413 relative to the bearing 404. The bearing 404 is in the form of a ball joint. When the drive arm 403 is driven so the bearing 413 moves in a circular path, the bearing moves longitudinally in the channels 408, as well as rotationally. The follower assembly 410 is provided with a gear rack 411 forward of the axle arrangement 406 from the arms 407. The rack 411 is preferably a sector gear and is preferably curved, having an inner edge curved in a circular arc with a radius approximately equal to its spacing from the center of rotation about the axle assembly 406 and an outer edge curved in an arc with a radius approximately equal to its spacing from the center of rotation about the axle assembly 406. The gear tooth surface 415 is beveled relative to the plane of rotation of the follower assembly 410. This accommodates its driving a pinion gear 416 mounted to the shaft 36 to which it is mounted. The gear 416 is a bevel gear that has gear teeth that mesh with the gear teeth of the rack 411. The shaft 36 is mounted in the housing 32 via bearings 59 as described above. The rack 411 rotates in two directions about the axle assemble 406, which effects oscillating rotation of the shaft 36, also in two directions. Thus, the follower assembly 410 converts one directional rotation of the motor 52 and drive arm 403 into two direction oscillatory rotation.

The term gear, bevel gear, curved gear rack, and gear rack as used herein includes both complete gears and gear segments.

Figure 22:
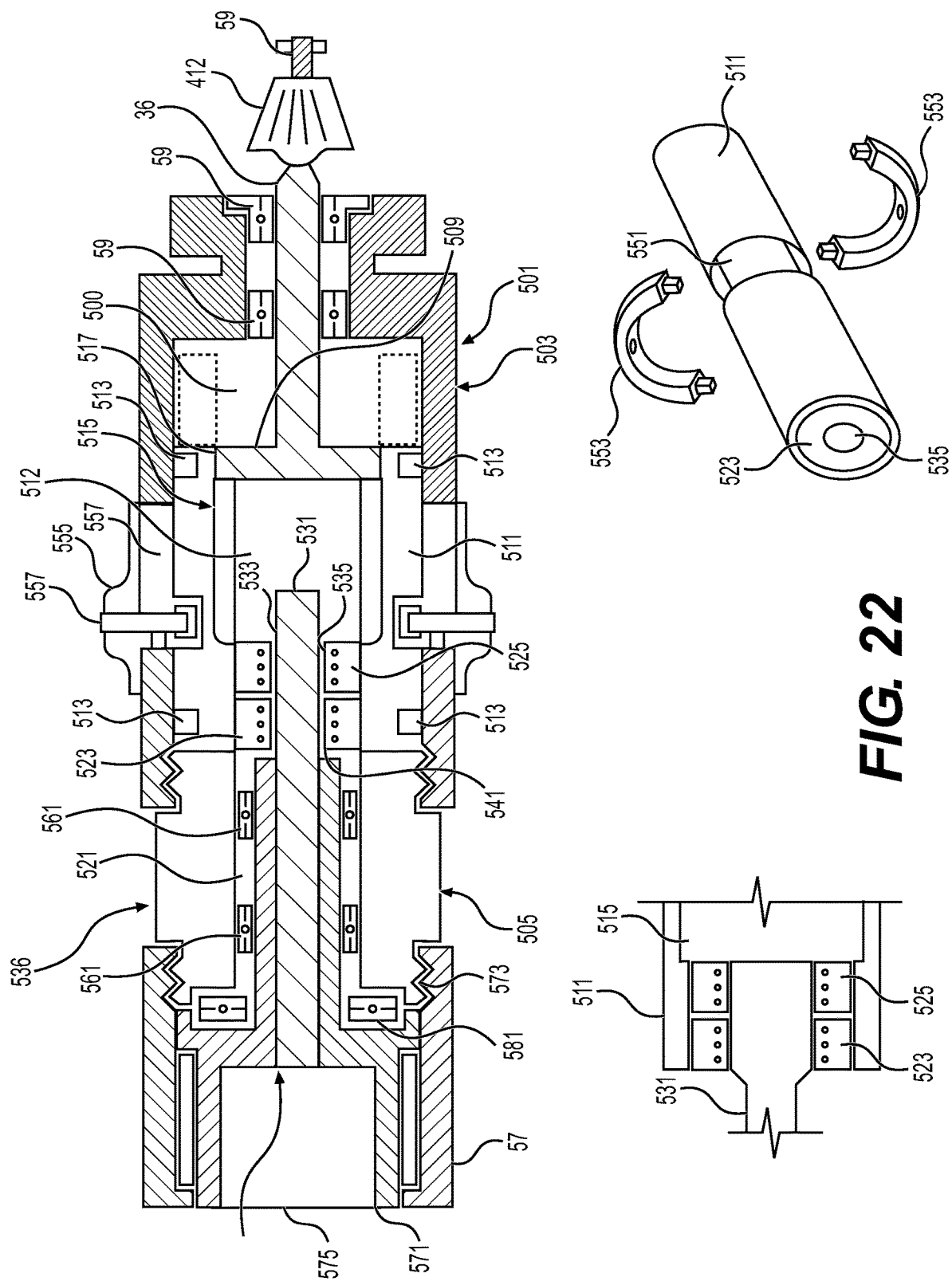
FIG. 22 includes a sectional view of two transmissions that are operable to provide oscillating rotary motion selectively in one of two directions or two unidirectional directions of a surgical device.

FIG. 22 illustrates a further embodiment of the present disclosure. It is configured to allow for multiple modes of operation of the output of the tool 30. It will allow for the above described outputs of the first shaft 36, in rotary oscillation shaft motion. The tool 30 is constructed to provide for both the above oscillating rotary operation of an end effector, and for unidirectional rotation of an end effector. The tool 30 includes a housing 32 and a motor 52 mounted in the housing. It also includes a first transmission 35 and a second transmission 536. The first transmission 35 is coupled to the motor 52 and is operable to selectively effect rotary oscillating motion of the first shaft 36 and of an end effector. The second transmission 536 is operable to selectively convert the oscillating rotation output of the first transmission 35 to unidirectional rotation of an end effector. The second transmission includes an output shaft 521 and coupling means such as coupler 571 configured to couple with an end effector. The output shaft 521 is coupled to the first shaft 36 and is fixed against relative rotation between the first shaft 36 and the output shaft 521, but allows relative longitudinal movement therebetween. The second transmission 536 includes at least one sprag clutch operable to allow the first driver to selectively effect oscillating rotation of the output shaft 521 and the coupler 571 and unidirectional rotation of the coupler in a selected unidirectional direction of rotation.

In a preferred embodiment, the first transmission 35 can utilize the first driver 37. In the preferred embodiment, housing 32 includes an enclosure 501 as part thereof, and has the nose 57 operably associated therewith. As shown, the enclosure 501 includes a proximal end sheath portion 503 and a distal end sheath portion 505. As shown, the nose 57 is at the distal end of the sheath portion 503 of the housing 501. As shown, the nose 57, and sheath portions 503, 505 are threadably connected, but other suitable connections can be provided. Additionally, the three described portions can be of a single piece construction. It is also noted that the enclosure 501 can be connected to the housing 32 in any suitable manner for a multi piece construction or can be integral therewith.

The shaft 36 is movably rotatably mounted in the enclosure 501. The shaft 36 is shown as mounted in the bearings 59, which are in turn mounted in the enclosure 501 in a bore 507. As illustrated, the shaft 36 has a flange 509 positioned on its free distal end. A sleeve 511 is mounted in the enclosure 501, preferably for both rotational and reciprocating longitudinal motion. One or more bearings 513, such as roller bearings, accommodate the movements of the sleeve 511 within the enclosure 501. The sleeve 511 is coupled to the shaft 36 such that the shaft 36 can effect the movement(s) of the sleeve 511. In one embodiment, the coupling can be via a splined connection with splines 515 projecting inwardly from an interior surface defining a through bore 512 of the sleeve 511 and splines 517 projecting outwardly from an exterior surface of the flange 509. The splines 517 interengage to accommodate rotational and reciprocating longitudinal motion of the sleeve 511.

Means is provided to effect coupling of the sleeve 511 to an output shaft 521 also carried by the enclosure 501. In the illustrated embodiment, the second transmission 536 includes a pair of sprag clutches 523 and 525. A sprag clutch is a one-way freewheeling clutch. In one direction, rotation between an inner race and an outer race is allowed; while in the opposite direction of rotation of an inner race to an outer race, relative rotation between the inner and outer race is prohibited. As shown, the sprag clutches 523, 525 are mounted in the bore 512 of the sleeve 511 with the outer races thereof being fixed against movement relative to the sleeve 511, while the inner races are permitted to move relative to the sleeve 511 as described below. The sprag clutches 523, 525 are also mounted to the output shaft 521 in a manner to allow relative movement longitudinally of the shaft 521. The sprag clutches 523, 525 are keyed to the shaft 521 to selectively prevent and allow relative rotation between their inner races in the shaft 521. The keyed mode of coupling can be provided by having a proximal free end portion 531 of the shaft 521 splined 533 on an outer surface while the inner surfaces of the inner races of the sprag clutches 523, 525 are also splined 535, allowing relative longitudinal movement of the sprag clutches 523, 525 to the shaft 521. As shown, the proximal end 531 of the shaft 521 has an enlarged diameter portion where the splines 533 are located and a decreased diameter portion 541 that is small enough to prevent contact of the shaft 521 with the inner race of the sprag clutches 523, 525. The sprag clutches 523, 525 are mounted in the sleeve 511 in longitudinally spaced apart relationship. The splines 533, 535 can have tapered lead in sections to facilitate their selectively interengagement.

The sleeve 511 is selectively longitudinally movable within the housing 501 to effect which sprag clutch 523, 525 will drive the output shaft 531. As shown, the sleeve 511 is provided with an exterior annular groove 551 opening outwardly. A split annular ring 553 is mounted in the groove 551 and fits within the enclosure 501. An operator 555 is positioned on the exterior of the housing 551 and is attached to the ring 553 as with a threaded fastener 557. The fastener 557 extends through an elongate slot 559 through the housing 501. The operator 555 is operable to selectively move the sleeve 511 longitudinally relative to the housing 501 and allows the sleeve to rotate within the housing. Means (not shown) such as a detent can associate the operator 555 with the enclosure 501 to selectively fix the operator in a selected position relative to the enclosure 501 that sets the operating mode.

The shaft 521 is rotatably mounted in the housing 501 as with bearings 561 mounted in the sheath portion 505 and on the shaft 521. The shaft 521 is provided with coupling means, designated generally 571 that are positioned in the nose 57. As shown, the nose 57 is mounted to the sheath portion 505 as by a threaded interengagement at 573. The means 571, as illustrated, includes a coupler 575 that can be in the form of a hex socket or square socket having detent means (not shown) to secure a surgical device 38 to the tool 30. In the illustrated structure, a thrust bearing 581 can be provided to reduce operational friction between the coupler 575 and the sheath portion 505.

In operation, as seen in FIG. 22, the motor 52 is actuated, which in turn drives the rack 411, which in turn drives the gear 412, which in turn effects reciprocating rotation of the shaft 36. The shaft 36 then effects rotation of the sleeve 511 in the enclosure 501. To effect intermittent rotation of the shaft 531 in a first direction, the sprag clutch 525 is engaged on the spline 533 of the shaft 531, as illustrated in FIG. 22. To effect intermittent rotation of the shaft 531 in a second and opposite direction, the sprag clutch 525 is moved longitudinally aft to disengage the shaft 531 and engage the other sprag clutch bearing 523 on the spline 533. This then effects intermittent rotation of the shaft 531 in the opposite direction. During the unidirectional rotations, as just described, there is a pause in the rotation while the rack 411 moves in its non-driving direction, which will provide an impact to the shaft 531 from the change in direction of rack 411 movement. In other words, the rack 411 drives during only one half of its complete motion cycle. This effects unidirectional motion either clockwise or counterclockwise of the shaft 531. To effect bidirectional oscillating rotation of the shaft 531, the operator 555 is moved to a position whereby both sprag clutches 523, 525 are engaged with the spline 533 of the shaft 531, allowing both sprag clutches 523, 525 to effect bidirectional oscillating rotation of the shaft 531. To effect selection of rotation of the shaft 531, the motor 52 will need to be deenergized to allow repositioning of a sprag clutch 523, 525 with the operator 555.

FIGS. 23A-23C and FIG. 24 illustrate a further embodiment of the tool 30, which is similar in operations to the tool described above in regard to FIG. 22 and includes a first transmission 35 and a second transmission 536 generally as described above. The tool 30 includes a housing 52, also as described above. The housing 52 includes an enclosure 601 as part thereof and has the nose 57 operably associated therewith. As shown, the enclosure 601 includes a sheath 603. As shown, the nose 57 is part of the housing 52 and located at the distal end of the sheath 603 of the enclosure 501. As shown, the nose 57 and sheath 603 are threadably connected, but other suitable connections can be provided. The sheath 603 is suitably mounted to portions of the housing 52.

A shaft 36 is operably coupled to the rack 411 via a gear 412 as described above. The shaft 36 can be rotatably mounted in a plurality of bearings 59. As shown, two of the bearings 59 are mounted in a bearing block 610 that is in turn mounted in sleeve 603, which is similar in construction and operation to the above described sleeve 511. An operator 655 is movably mounted on the sleeve 603, and is similar in operation and construction to the operator 555. The operator 655 includes a finger 656 that is movable along the length of the slot 612 for a purpose described below.

The shaft 36 is coupled to a second shaft 631 to effect oscillating rotation thereof. The distal end portion 632 of the shaft 36 keys to the second shaft 631 in a manner to prevent relative rotation, while allowing relative longitudinal movement therebetween. As shown, the distal end portion 632 of shaft 36 is generally square at 636 and is received in a corresponding square bore 634 of the shaft 631. This arrangement allows for relative longitudinal movement between the shafts 36 and 631 while preventing relative rotation. The shaft 631 is mounted in at least one, and preferably a pair of sprag clutches 623, 625. The use of a single sprag clutch will permit only one direction of unidirectional rotation, while a pair of sprag clutches will permit unidirectional rotation of an end effector in two directions. The sprag clutches 623, 625 are secured in a bore 637 in the coupling means 671 in a manner to eliminate relative movement therebetween. An idle bearing 626 also rotatably supports the shaft 631 and is mounted in the bore 637 coupling means 671. As shown, the shaft 631 has an enlarged diameter portion 634 for a purpose later described. A thrust bearing 673 can be provided to reduce friction when a coupling means 671 is being operated as described below. The operator 655 couples to the shaft 631 via a bearing 675 fixed to the shaft 631. A retainer portion 677 of the operator 655 couples to the bearing 675. The bearing 675 can be attached to the shaft 631 via a retainer 679, such as a C-clip.

Figure 23B:
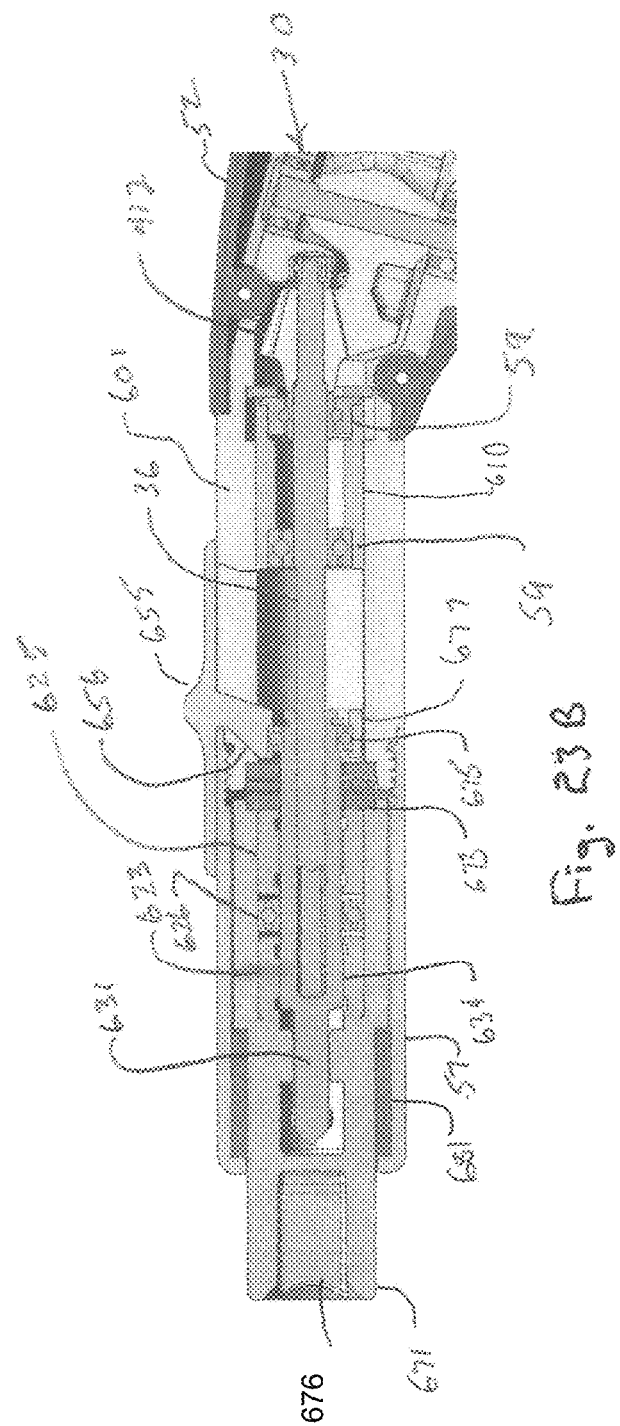
Figure 23C:
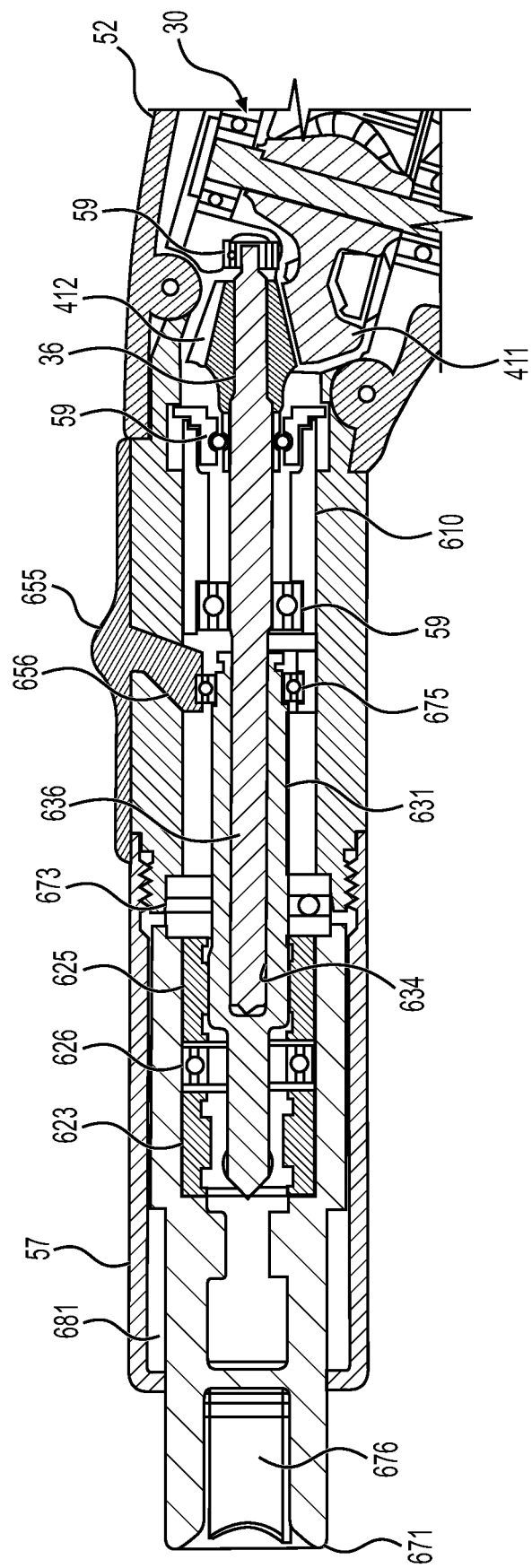
Figure 24:
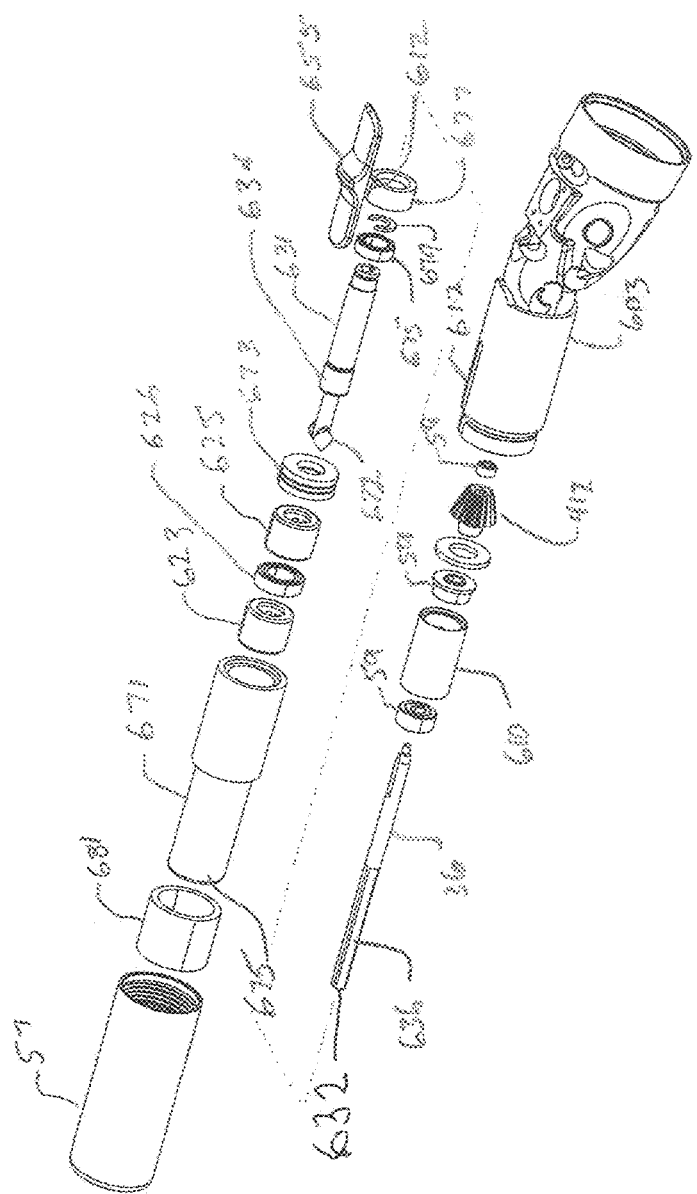
FIG. 24 is an exploded perspective view of the transmissions of FIGS. 23A-C.

The shaft 631 selectively couples to the coupling means 671 to provide for three different modes of driving of the coupling means 671 by the shaft 36. As seen in FIG. 23A, the coupling means 671 is drivingly coupled to the shaft 631 to provide a direct drive to effect bidirectional oscillating rotation of the coupling means 671. The coupling can be by a splined connection, a key connection or the like at 672, but allows relative movement between the shaft 631 and the coupling means 671. This engagement should preferably be made when the motor 52 is deenergized. Movement of the shaft 631 from the mid position, shown in FIG. 23A, to a forward position, as seen in FIG. 23B, through operation of the operator 655, disengages the spline connection and moves the enlarged diameter portion 634 into the sprag clutch 623. The sprag clutch 623 is oriented such that it will drive the coupling means 671 only in one direction during one half of a complete cycling of the bidirectional rotation of the shaft 36 by the rack 411. Upon movement of the shaft 631 to a rear position with the operator 655, as seen in FIG. 23C, the enlarged diameter portion 634 moves into engagement with the sprag clutch 625; which is oriented for freewheeling in the opposite direction of that of sprag clutch 623. This will then effect rotation in only one direction during one half of a complete rotation cycle of the shaft 36, and is directionally opposite to that described when the sprag clutch 623 is operational. The shaft 631 functions as an inner race for the sprag clutches 623, 625. As described above, a change in direction of rotation of the shaft 36 will provide an impact to the coupling means 671 and an attached surgical device 38.

As shown, the coupling means 671 is rotatably mounted in the nose 57, as with a sleeve bearing 681. The bearings 681, 673 capture the coupling means 671 therebetween, limiting its longitudinal movement. The coupling means 671 can be in any suitable form and can include a socket 676 similar in construction and operation to the socket 575 described above.

All patents and publications mentioned in this specification are indicative of the levels of those skilled in the art to which the disclosure pertains. All patents and publications are herein incorporated by reference to the same extent as if each individual publication was specifically and individually indicated to be incorporated by reference.

It is to be understood that while a certain form of the disclosure is illustrated, it is not to be limited to the specific form or arrangement herein described and shown. It will be apparent to those skilled in the art that various changes may be made without departing from the scope of the disclosure and the disclosure is not to be considered limited to what is shown and described in the specification and any drawings/figures included herein.

One skilled in the art will readily appreciate that the present disclosure is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the disclosure and are defined by the scope of the appended claims. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in the art are intended to be within the scope of the following claims.

What is claimed is:

1. A surgical tool operable to selectively provide oscillating rotation and unidirectional rotation of an end effector, the surgical tool including:
    a housing;
    a motor mounted in the housing;
    a first transmission including a first driver and a first shaft coupled to the motor and operable to effect oscillating rotation of the first shaft;
    a second transmission including an output shaft and a coupler configured to couple with an end effector, the output shaft being coupled to the first shaft and being fixed against relative rotation between the first shaft and the output shaft but allowing relative longitudinal movement therebetween, the second transmission including at least one sprag clutch operable to allow the first driver to selectively effect oscillating rotation of the second shaft and the coupler and unidirectional rotation of the coupler in a selected direction of rotation; and
    an operator movably mounted to the housing and coupled to the output shaft to effect longitudinal movement of the output shaft relative to the first shaft to selectively effect the rotational oscillation of the output shaft and the coupler and the unidirectional rotation of the coupler.

2. The surgical tool of claim 1, wherein the second transmission includes a pair of sprag clutches, each sprag clutch being oriented relative to the output shaft to selectively effect rotation of the output shaft in opposite rotational directions.

3. The surgical tool of claim 2, wherein the motor comprises a shaft operable to rotate in a single direction.

4. The surgical tool of claim 2, wherein the output shaft comprises a first portion sized to engage a the sprag clutch and a second portion sized to be free of engagement with a the sprag clutch.

5. The surgical tool of claim 4, wherein the operator is operable to move the output shaft axially relative to the first shaft and the coupler between three positions.

6. The surgical tool of claim 5, wherein the sprag clutches are mounted in a bore in the coupler in longitudinally spaced relationship.

7. The surgical tool of claim 6, wherein the output shaft is selectively axially movable relative to the first shaft between a plurality of positions and in a first position of the plurality of positions the output shaft is coupled to effect direct drive engagement to effect oscillating rotation of the coupler.

8. The surgical tool of claim 7, wherein the output shaft is selectively drivingly coupled to the coupler through one of the sprag clutches through movement of the operator to selectively effect unidirectional rotation of the coupler.

9. The surgical tool of claim 2, wherein the second transmission is operable to selectively convert oscillating rotation of the first shaft to unidirectional rotation of the coupler.

10. The surgical tool of claim 9, wherein the second transmission is operable to selectively convert oscillating rotation of the first shaft to intermittent unidirectional rotation of the coupler.

11. A surgical tool operable to selectively provide oscillating rotation and unidirectional rotation of an end effector, the surgical tool including:
    a housing;
    a motor mounted in the housing;
    a first transmission including a first driver and a first shaft coupled to the motor and operable to effect oscillating rotation of the first shaft;
    a second transmission including an output shaft and a coupler configured to couple with an end effector, the output shaft being coupled to the first shaft and being fixed against relative rotation between the first shaft and the output shaft but allowing relative longitudinal movement therebetween, wherein the second transmission includes a pair of sprag clutches, each sprag clutch being oriented relative to the output shaft to selectively effect rotation of the output shaft in opposite rotational directions; and an operator movably mounted to the housing and coupled to the output shaft to effect longitudinal movement of the output shaft relative to the first shaft to selectively effect the rotational oscillation of the output shaft and the coupler and the unidirectional rotation of the coupler.

12. The surgical tool of claim 11, wherein the motor comprises a shaft operable to rotate in a single direction.

13. The surgical tool of claim 11, wherein the output shaft comprises a first portion sized to engage a sprag clutch of the pair of sprag clutches and a second portion sized to be free of engagement with a the sprag clutch.

14. The surgical tool of claim 13, wherein the operator is operable to move the output shaft axially relative to the first shaft and the coupler between three positions.

15. The surgical tool of claim 14, wherein the sprag clutches are mounted in a bore in the coupler in longitudinally spaced relationship.

16. The surgical tool of claim 15, wherein the output shaft is selectively axially movable relative to the first shaft between a plurality of positions and in a first position of the plurality of positions the output shaft is coupled to effect direct drive engagement to effect oscillating rotation of the coupler.

17. The surgical tool of claim 16, wherein the output shaft being selectively drivingly coupled to the coupler through one of the sprag clutches through movement of the operator to selectively effect unidirectional rotation of the coupler.

18. The surgical tool of claim 11, wherein the second transmission is operable to selectively convert oscillating rotation of the first shaft to unidirectional rotation of the coupler.

19. The surgical tool of claim 18, wherein the second transmission being operable to selectively convert oscillating rotation of the first shaft to intermittent unidirectional rotation of the coupler.

* * * * *